United States Patent [19]
Sugarman et al.

[11] Patent Number: 6,056,926
[45] Date of Patent: May 2, 2000

[54] APPARATUS AND METHOD FOR PARALLEL COUPLING REACTIONS

[75] Inventors: Jeffrey H. Sugarman, Sunnyvale; Richard P. Rava; Haim Kedar, both of Palo Alto, all of Calif.

[73] Assignee: Affymax Technologies N.V., Greenford, United Kingdom

[21] Appl. No.: 08/685,273

[22] Filed: Jul. 23, 1996

Related U.S. Application Data

[60] Continuation of application No. 08/468,672, Jun. 6, 1995, abandoned, which is a division of application No. 08/149,675, Nov. 2, 1993, Pat. No. 5,503,805.

[51] Int. Cl.⁷ .............................. C08F 2/00; G05B 17/00; C12N 15/00; A61K 38/00
[52] U.S. Cl. .......................... 422/131; 422/110; 422/116; 530/333; 530/334; 525/54.1; 525/54.11
[58] Field of Search .................................... 422/131, 236, 422/62, 100, 110, 116; 935/86–88; 530/333, 334, 335, 338; 525/54.1, 54.11

[56] References Cited

U.S. PATENT DOCUMENTS

| | | | |
|---|---|---|---|
| 4,182,654 | 1/1980 | Royer | 435/272 |
| 4,315,074 | 2/1982 | Royer | 435/70 |
| 4,517,338 | 5/1985 | Urdea et al. | 525/54.11 |

(List continued on next page.)

FOREIGN PATENT DOCUMENTS

| | | | |
|---|---|---|---|
| 0 392 546 A2 | 12/1990 | European Pat. Off. | C12Q 1/68 |
| WO 90/00626 | 1/1990 | WIPO | C12Q 01/68 |
| WO 90/14441 | 11/1990 | WIPO | C12Q 1/68 |
| WO 90/15070 | 12/1990 | WIPO | C07K 1/04 |
| WO/91/17823 | 11/1991 | WIPO . | |
| WO 92/00091 | 1/1992 | WIPO | A61K 37/02 |
| WO 92/03461 | 3/1992 | WIPO | C07H 17/00 |
| WO 92/06176 | 4/1992 | WIPO | C12N 1/24 |
| WO 92/10092 | 6/1992 | WIPO | A01N 1/02 |
| WO 93/20242 | 10/1993 | WIPO | C12Q 1/70 |
| WO 94/02515 | 2/1994 | WIPO | C07K 17/16 |
| WO 94/08051 | 4/1994 | WIPO | C12Q 1/68 |

OTHER PUBLICATIONS

*Advances in Analytical Chemisrty and Instrumentation*, Charles N. Reilley, Ed., John Wiley & Sons, Inc., 1964, pp. 56–59.

Arnold et al., Mar. 15, 1991, *Optics Letters* 16(6):420–422 *Room–temperature microparticle–based persistent spectral hole burning memory*.

Baldwin et al., 1990, *Tetrahedron* 46(19):6879–6884 *New photolabile phosphate protecting groups*.

Barr et al., 1986, *BioTechniques* 4(5):428–432 *7–Deaze–2'–deoxyguanosine–5'–triphosphate: Enhanced resolution in M13 dideoxy sequencing*.

Bashkin et al., 1991, *J. Org. Chem.* 56:3168–3176 *Synthesis and characterization of oligonucleotide peptides*.

Borchardt et al., 1994, *J. Am. Chem. Soc.* 116:373–374 *Synthetic receptor binding elucidated with an encoded combinatorial library*.

(List continued on next page.)

*Primary Examiner*—Christopher Kim
*Attorney, Agent, or Firm*—Lauren L. Stevens; Vernon A. Norviel

[57] ABSTRACT

A device and method for efficiently synthesizing diverse molecular products on substrates. A parent vessel 200 contains a suspension of substrates. The suspension is pressurized with argon and transferred to a plurality of reaction vessels 201–209 in one or more reaction vessel banks where monomer addition reactions take place. Optionally, the substrates may be tagged with a tag monomer. A vortexing motor 300 vortexes the contents of reaction vessels 201–209 during monomer addition reactions to enhance synthesis. After the desired monomer and/or tag monomer addition reaction, the suspension is pressurized with argon and transferred back to parent vessel 200 for mixing. Thereafter, the suspension may be pressurized with argon and reallocated among reaction vessels 201–209 for further synthesis.

14 Claims, 24 Drawing Sheets

Microfiche Appendix Included
(3 Microfiche, 200 Pages)

U.S. PATENT DOCUMENTS

| | | |
|---|---|---|
| 4,587,044 | 5/1986 | Miller et al. .............................. 530/211 |
| 4,631,211 | 12/1986 | Houghten ................................. 428/35 |
| 4,671,941 | 6/1987 | Niina et al. .............................. 422/131 |
| 4,671,947 | 6/1987 | Niina et al. .............................. 422/131 |
| 4,701,304 | 10/1987 | Horn et al. ............................... 422/62 |
| 4,704,256 | 11/1987 | Hood et al. ............................... 422/68 |
| 4,713,326 | 12/1987 | Dattagupta et al. ....................... 435/6 |
| 4,746,490 | 5/1988 | Saneii ....................................... 422/62 |
| 4,755,558 | 7/1988 | Kalbag ................................. 525/54.1 |
| 4,794,150 | 12/1988 | Steel .................................. 525/54.11 |
| 4,812,654 | 3/1989 | Royer ..................................... 435/272 |
| 4,818,681 | 4/1989 | Dattagupta ............................... 435/6 |
| 4,833,092 | 5/1989 | Geysen ................................... 436/501 |
| 4,855,225 | 8/1989 | Fung et al. ................................. 435/6 |
| 4,965,188 | 10/1990 | Mullis et al. .............................. 435/6 |
| 5,143,854 | 9/1992 | Pirrung et al. ......................... 436/518 |
| 5,182,366 | 1/1993 | Hueber et al. . | |
| 5,252,296 | 10/1993 | Zuckermann et al. .................. 422/116 |
| 5,264,563 | 11/1993 | Huse ..................................... 536/25.3 |
| 5,324,483 | 6/1994 | Cody et al. ............................. 422/131 |

OTHER PUBLICATIONS

Brenner et al., 1992, *Proc. Natl. Acad. Sci. USA* 89:5381–5383 *Encoded combinatorial chemistry*.

Crick et al., 1957, *Proc. Natl. Acad. Sci. USA* 43:416–421 *Codes without commas*.

Cwirla et al., 1990, *Proc. Natl. Acad. Sci. USA* 87:6378–6382 *Peptides on phage: A vast library of peptides for indentifying ligands*.

Eritja et al., 1991, *Tetrahedron* 47(24):4113–4120 *Synthesis of defined peptide–oligonucleotide hybrids containing a nuclear transport signal sequence*.

Fodor et al., 1991, *Science* 251:767–773 *Light–directed, spatially addressable parallel chemical synthesis*.

Frank and Doring, 1988, *Tetrahedron* 44(19):6031–6040 *Simultaneous multiple peptide synthesis under continuous flow conditions on cellulose paper discs as segmental solid supports*.

Frank et al., 1983, *Nuc. Acids. Res.* 11(13):4365–4377 *A new general approach for the simultaneous chemical synthesis of large numbers of oligonucleotides: Segmental solid supports*.

Frank et al., 1990, *Peptides* (Giralt & Andreu, eds., Escom Science Pub.), pp. 151–152 *Facile and rapid 'spot–synthesis' of large numbers of peptides on membrane sheets*.

Furka et al., Jul. 10–15, 1988, *14th Int'l Congress of Biochemistry*, Prague, Czechoslovakia, Abstract No. FR:013 *Proteins and nucleic acids in three dimensions: Cornucopia of peptides by synthesis*.

Furka et al., Aug. 15–19, 1988, *Symp. on Medicinal Chem.*, Budapest, Hungary, Abstract No. P–168, p. 288 *More peptides by less labour*.

Furka et al., 1991, *Int. J. Peptide Protein Res.*, 37:487–493 *General method for rapid synthesis of multicomponent peptide mixtures*.

Geysen et al., 1987, *J. Immunol. Meth.*, 102:259–274 *Strategies for epitope analysis using peptide synthesis*.

Geysen et al., 1984, *Proc. Natl. Acad. Sci. USA*, 81:3998–4002 *Use of peptide synthesis to probe viral antigens for epitopes to a resolution of a single amino acid*.

Haralambidis et al., 1990, *Nuc. Acids Res.* 18(3):493–505 *The synthesis of polyamide–oligonucleotide conjugate molecules*.

Hayakawa et al., 1990, *J. Am. Chem. Soc.* 112:1691–1696 *The allylic protection method in solid–phase oligonecleotide synthesis: An efficient preparation of solid–anchored DNA Oligomers*.

Hodgson, 1992, *Bio/Technology* 10:973–974 *Receptor screening and the search for new pharmaceuticals*.

Houghten et al., 1991, *Nature* 354:84–86 *Generation and use of synthetic peptide combinatorial libraries for basic research and drug discovery*.

Houghten, 1985, *Proc. Natl. Acad. Sci. USA* 82:5131–5135 *General method for the rapid solid–phase synthesis of large numbers of peptides: Specificity of antigen–antibody interaction at the level of individual amino acids*.

Juby et al., 1991, *Tetrahedron Letters* 32(7):879–882 *Facile preparation of 3' oligonucleotide–peptide conjugates*.

Kaiser et al., 1989, *Science* 243:187–192 *Peptide and protein synthesis by segment synthesis–condensation*.

Kerr et al., 1993, *J. Am. Chem Soc.*, 115:2529–2531 *Encoded combinatorial peptide libraries containing non–natural amino acids*.

Lam et al., 1991, *12th Amer. Pep. Symp.*, Abstract LW3 *Rapid selection and structure determination of acceptor binding ligands from a large synthetic peptide library*.

Lam et al., 1991, *Nature* 354:82–84 *A new type of synthetic peptide library for indentifying ligand–binding activity*.

Needels et al., 1993, *Proc. Natl. Acad. Sci. USA*, 90:10700–10704 *Generation and screening of an oligonucleotide–encoded synthetic peptide library*.

Nikolaiev et al., 1993, *Peptide Research*, 6(3):161–170 *Peptide–encoding for structure determination of nonsequenceable polymers within libraries synthesized and tested on solid phase supports*.

Ohlmeyer et al., 1993, *Proc. Natl. Acad. Sci. USA*, 90:10922–10926 *Complex synthetic chemical libraries indexed with molecular tags*.

Tjoeng et al., 1990, *Int. J. Pept. Protein Res.* 35:141–146 *Multiple peptide synthesis using a single support (MPS3)*.

Van der Zee et al., 1989, *Eur. J. Immunol.* 19:43–48 *Efficient mapping and characterization of a T cell epitope by the simultaneous synthesis of multiple peptides*.

6,056,926

APPARATUS AND METHOD FOR PARALLEL COUPLING REACTIONS

This is a continuation of application Ser. No. 08/468,672 filed Jun. 6, 1995, abandoned, which is a Division of application Ser. No. 08/149,675 filed Nov. 2, 1993, now U.S. Pat. No. 5,503,805.

MICROFICHE APPENDIX

This specification includes microfiche Appendix 1 having 3 sheets with 200 frames.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD OF THE INVENTION

The present invention relates to the field of chemical synthesizers. More particularly, in one embodiment, the invention provides a reaction device and technique for synthesizing diverse chemical products on solid supports such as beads.

BACKGROUND OF THE INVENTION

Diverse chemical products find a wide variety of uses such as in drug discovery, genetic studies, and the like. Exemplary of the diverse chemical products that are useful in scientific studies are peptides, oligonucleotides, and other related materials.

The synthesis of diverse chemical products has often created difficulties, however. For example, it is often desirable to synthesize diverse collections of molecules on a plurality of solid supports such as beads. Examples of the use of beads with diverse molecular products synthesized thereon are disclosed in, for example, the following applications, incorporated herein by reference for all purposes: U.S. application Ser. No. 07/876,792, filed on Apr. 29, 1992, now U.S. Pat. No. 5,541,061; U.S. application Ser. No. 07/762,522, filed on Sep. 18, 1991, now abandoned; U.S. application Ser. No. 07/946,239, filed on Sep. 16, 1992, now U.S. Pat. No. 5,770,348; and U.S. application Ser. No. 08/146,866, filed on the same day as the present application (Attorney Docket No. 11509-121/1007.2), now U.S. Pat. No. 5,639,603.

While meeting with substantial success, the techniques described above have also met with certain limitations. For example, when the synthesis of diverse products takes place on beads, many manual manipulations of such beads becomes necessary. For example, in U.S. application Ser. No. 07/876,792, filed on Apr. 29, 1992, now U.S. Pat. No. 5,541,061, incorporated by reference herein for all purposes, one must suspend a collection of beads in a carrier, divide the beads, perform monomer addition reactions on the divided sets of beads, sometimes redivide and selectively recombine the beads thus synthesized, mix the recombined beads, and repeat the process. When large numbers of monomers are involved and when the reactions involve many monomer addition steps, manual techniques become extremely tedious. In addition, the "accounting" for the many products that have been synthesized becomes a daunting task.

From the above, it is seen that improved techniques of synthesizing diverse chemical products on beads or other similar substrates are desired.

SUMMARY OF THE INVENTION

The present invention provides a device and method for rapidly and efficiently synthesizing diverse molecular products. According to specific aspects of the invention, diverse polymers are synthesized on substrates such as glass beads. Optionally, the beads may be simultaneously "tagged" during the synthesis reactions with a molecular tag. Merely by way of example, the synthesized molecules on the beads may comprise peptides, while the molecular tags may comprise oligonucleotides. Of course, other molecular products may also be synthesized using the techniques described herein whenever a molecule has a basic "building block" common to other related molecules. Examples include benzodiazapines, prostaglandins, and beta turn mimetics.

According to one embodiment of the invention, a parent vessel is used to mix bead suspensions. The mixed beads are distributed through a common manifold to a plurality of separate reaction vessels. In the reaction vessels, the beads are exposed to different, selected monomers, which react on the beads to be coupled thereto, preferably covalently. The beads may, optionally, be exposed to chemical "tags" which also couple, covalently or otherwise, to the beads. The beads are then recombined through the manifold back to the parent vessel and mixed. The mixed bead suspension is then again divided among the plurality of reaction vessels, and the process of monomer addition, bead mixing, and redistribution continues. The process results in the formation of a collection of beads or other substrates with a diverse set of molecules formed on the surfaces thereof.

According to one aspect of the invention, the invention includes an apparatus and a method for synthesizing diverse molecules on substrates. The substrates are distributed to selected reaction vessels from a parent vessel. Reagents are then introduced into the reaction vessels to synthesize a portion of the molecules. The substrates are then moved to the parent vessel for mixing. The substrates are then redistributed to the reaction vessels for further synthesis. The cycles continue until a desired set of molecules are synthesized. During synthesis, the entire synthesizer is sealed from the external atmosphere.

A further understanding of the nature and advantages of the invention may be had with reference to the description and drawings below.

DESCRIPTION OF THE SPECIFIC EMBODIMENTS

Figure 1:
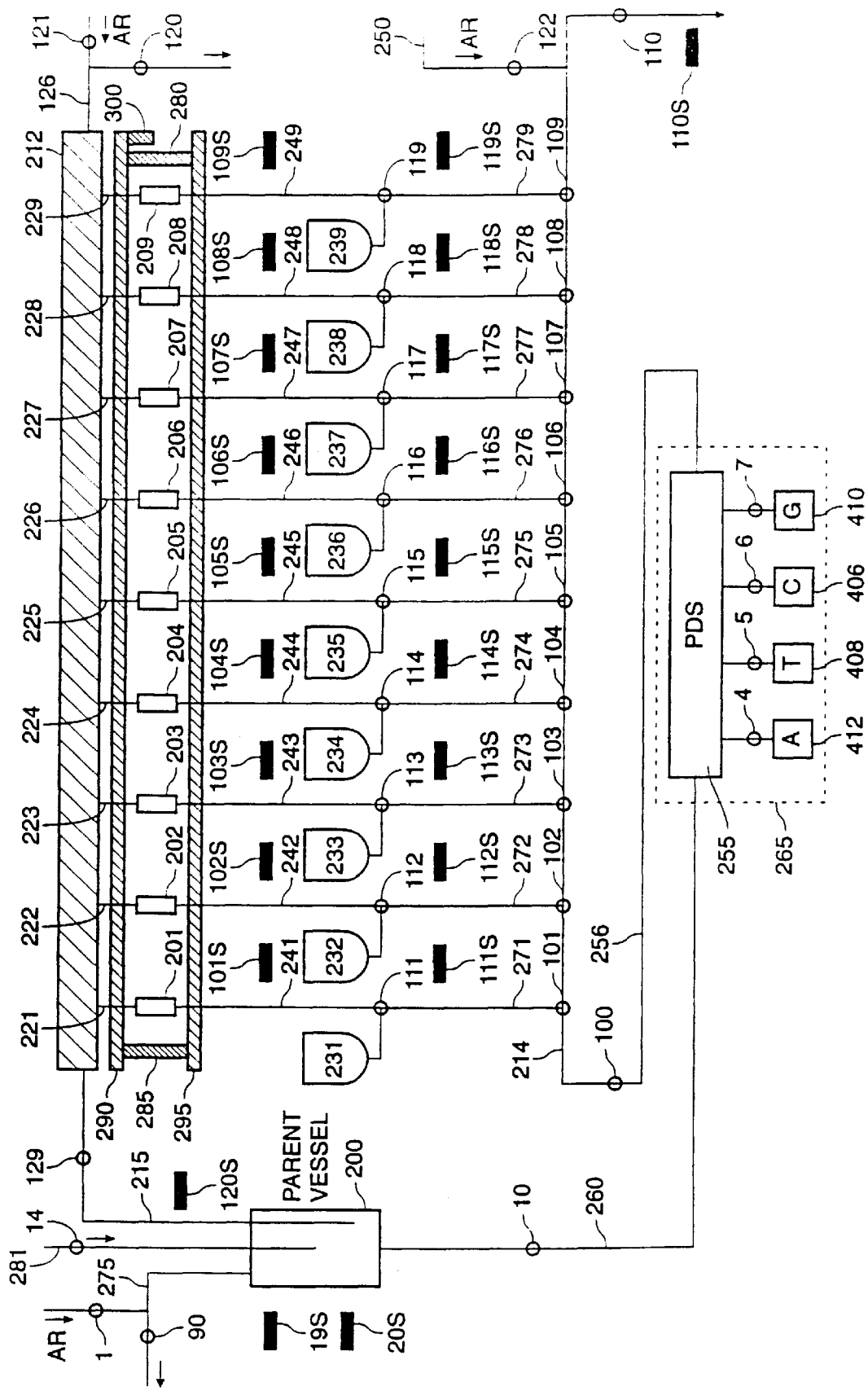
FIG. 1 shows a schematic diagram of the synthesizer of the present invention.

The present invention is used to synthesize collections of diverse molecules. Although the invention is illustrated primarily with regard to the synthesis of oligonucleotides and peptides, the invention is not so limited. The invention will find application in the synthesis of materials such as polysaccharides, phospholipids, polyurethanes, benzodiazapines, prostaglandins, and beta turn mimetics, and other materials. Cyclic materials may be formed as disclosed in U.S. Pat. No. 5,242,974 (Holmes), incorporated herein by reference.

The use and synthesis of diverse materials such as oligonucleotides and peptides is disclosed in detail in the following copending applications, which are incorporated herein by reference for all purposes: U.S. application Ser. No. 07/876,792, filed on Apr. 29, 1992, now U.S. Pat. No. 5,541,061; U.S. application Ser. No. 07/762,522, filed on Sep. 18, 1991, now abandoned; U.S. application Ser. No. 07/946,239, filed on Sep. 16, 1992, now U.S. Pat. No. 5,770,358; and U.S. application Ser. No. 08/146,886, filed on the same day as the present application (Attorney Docket No. 11509-121/1007.2), now U.S. Pat. No. 5,639,603.

In general, the present invention provides for the synthesis of diverse materials on a solid substrate. By way of example, the present invention utilizes beads such as those made from glass, resins, plastics, or the like. Examples of a the synthesis of diverse peptides are discussed below to provide a framework for the discussion of the synthesizer.

As used herein, monomers include the set of small molecules which can be joined together to form a polymer. The set of monomers includes but is not restricted to, for example, the set of common L-amino acids, the set of D-amino acids, the set of synthetic amino acids, the set of nucleotides, and the set of pentoses and hexoses. Furthermore, monomers refer to any member of a basis set for synthesis of a polymer. For example, dimers of L-amino acids form a basis set of 400 monomers for synthesis of polypeptides. Different basis sets of monomers may be used at successive steps in the synthesis of a polymer.

The invention will utilize a plurality of substrates, referred to as "S," on which synthesis reactions take place. The substrates are optionally provided with a linker molecule "L" on which coupling reactions take place. The substrates are divided and reacted with diverse monomers, such as "A" and "B" to form collections of, for example, the following substrates:

S-A and S-B

Thereafter, the substrates are recombined, mixed, and divided again. After such mixing and dividing steps, two or more collections of substrates are formed, each containing both S-A and S-B.

Additional coupling reactions then take place. For example, the pooled products above may be reacted with monomers C and D to form the following collections of products:

1. S-A-C S-A-D
2. S-B-C S-B-D

From even the above simple example it becomes apparent that such synthesis techniques rapidly create large collections of diverse products. By carefully planning the synthesis of such diverse collections of molecules and/or by providing for the parallel synthesis of tags on such substrates, the substrates will find use in a variety of applications. For example, such substrates will find application in a wide range of fields including drug discovery, genetic sequencing, and the like. The present invention provides devices and methods that may efficiently generate substrates for these uses.

1. General

FIG. 1 illustrates a device used to synthesize diverse collections of molecules. The device includes a parent mixing vessel 200 coupled to a plurality of reaction vessels 201–209 by a top common manifold 212 and tubes 215, and 221–229. Top common manifold 212 couples to tubes 221–229 and 215. Reaction vessels 201–209 also selectively couple to monomer addition reagent supply reservoirs 231–239 via valves 111–119 and tubes 241–299. A pressurized delivery system (PDS) 265 is coupled to both parent vessel 200 and reaction vessels 201–209 via tubes 260 and 256 respectively.

A synthesis reaction begins when a bead suspension is transferred from parent vessel 200 to reaction tubes 201–209. A valve 129 opens (all valves are closed as default), and the bead suspension enters top common manifold 212 from parent vessel 200 through tube 215. The bead suspension is thereafter distributed among reaction vessels 201–209 through tubes 221–229. Selected reagents from monomer reservoirs 231–239 then enter respective reaction vessels 201–209 through respective tubes 241–249. Coupling reactions then take place inside reaction vessels 201–209 on beads contained therein.

FIG. 1 shows pressurized delivery system 265 coupled to parent vessel 200 via a tube 260. Pressurized delivery system 265 delivers pressurized reagents to parent vessel 200 from delivery system 265 via tube 260 when valve 10 and vent valve 90 open.

Pressurized delivery system 265 is also coupled to reaction vessels 201–209 through a tube 256, an isolation valve 100, lower manifold valves 101–109, lower tubes 271–279, injection valves 111–119, and tubes 241–249. To deliver a reagent from PDS 265 to selected reaction vessels 201–209, the pressurized reagent enters tube 256 and a lower manifold 214 through open valve 100. Thereafter, the pressurized reagent is forced up selected tubes 271–279 through selected open valves 101–109. The pressurized reagent is then forced into selected reaction vessels 201–209 through selected tubes 241–249.

To deliver a reagent from, for example, a given monomer reservoir 231 to a respective reaction vessel 201, a quantity of pressurized activating solution from PDS 265 is forced into tube 256, into lower manifold 214, and up tube 271. At an appropriate moment, a quantity of monomer reagent from monomer reservoir 231 is injected into the stream of activating solution travelling up tube 271. Following the reagent injection, the stream of solution including the monomer reagent injected from reagent reservoir 231 enters reaction vessel 201 through a tube 241 to participate in the coupling reactions.

To optionally tag the beads inside selected reaction vessels 201–209 with a monomer from monomer reservoirs 406–412, a pressurized tag monomer reagent from monomer reservoirs 406–412 enters a common manifold 255 of PDS 265 through an open valve 4–7. Thereafter, the pressurized tag monomer and an appropriate activation reagent enter lower manifold 214 through open valve 100 and tube 256. The pressurized monomer tagging reagent and its appropriate activation reagent travel up selected tubes 271–279 and 241–249 through selected open valves 101–109 into selected reaction vessels 201–209 where the synthesis of tags on beads takes place.

After desired monomer and/or tag addition reactions, the bead suspension in reaction vessels 201–209 is transferred back to parent vessel 200 for pooling and mixing. To move the bead suspension from reaction vessels 201–209 to parent vessel 200, the bead suspension is pressurized with argon from tube 250 via open valve 122 and 101–109. Valves 100 and 110 are closed, thereby pushing the pressurized bead suspension into tubes 221–229, top common manifold 212, tube 215 through open valve 129, and finally parent vessel 200. In parent vessel 200, the bead suspension is mixed in preparation for reallocation among reaction vessels 201–209 to further synthesize the desired set of molecules.

FIG. 1 also shows nonconcentric agitators 280 and 285 coupled to a top reaction vessel bracket 290 and a bottom reaction vessel bracket 295. Top reaction vessel bracket 290 is held stationary while bottom reaction vessel bracket 295 is permitted to follow the motion of nonconcentric agitators 280 and 285. Each nonconcentric agitator cooperates with a vortexing motor 300 to exert an agitation force on bottom vessel bracket 295 and the bottom end of reaction vessels 201–209. Since the tubes between the brackets are flexible, this agitation force causes the contents of each individual reaction vessel 201–209 to vortex inside the reaction vessel thereby enhancing synthesis reactions.

Top common manifold 212 connects to tube 215 at one end to provide a conduit for transferring material between parent vessel 200 and top common manifold 212. At the other end, top common manifold 212 connects to a tube 126. Tube 216 provides pressurized argon to top common manifold 212 through a valve 121. Tube 216 also allows top common manifold 212 to vent its contents through a valve 120.

Two capacitive sensors 90S and 99S are located near the exterior surface of parent vessel 200 to detect the level of liquid in parent vessel 200. If a fluid exists within the detection envelope of a capacitive sensor, that capacitive sensor is turned on. Conversely, the capacitive sensor is off if no fluid exists within the detection envelope.

Sensors 101S–119S are optical sensors for detecting the presence of a fluid within a substantially translucent tube. These optical sensors are on when a column of fluid is present in the tube. The optical sensors are off when no fluid is detected.

Likewise, an acoustic sensor 120S detects the presence of a fluid in its detection envelope. Fluid, including bead suspension, flowing through a tube which has been placed in the acoustic sensor's detection envelope turns acoustic sensor 120S on. Conversely, acoustic sensor 120S is off when no fluid is present in the tube which has been placed in the detection envelope of the sensors. Acoustic sensor is used for sensor 120S because optical sensors cannot reliably distinguish, under certain conditions, between an empty translucent teflon tube and a translucent teflon tube containing a bead suspension. Further, although an acoustic sensor is chosen for sensor 120S, any sensor which can distinguish the difference between an empty tube and a tube filled with either a fluid or a bead suspension may be used.

Because acoustic sensors are fairly costly relative to other types of sensor such as optical sensors, there is only one acoustic sensor 120S per synthesizer.

The reaction vessel bank is designed such that there is only one or fewer valve between the parent vessel and the reaction vessels. In fact, valve 129 is optional. This design is advantageous because some polymers are temperature sensitive and may be adversely affected by the heat generated by the valves during operation. Furthermore, the mechanical opening and closing action of valves may damage the fragile beads and the synthesized polymers. Accordingly, it is desirable to reduce the number of valves through which the bead suspension must traverse.

As discussed earlier, the valves used in this embodiment are closed in their default state. Absent a specific command to open, the valves always remain in this default closed state.

2. Mechanical Components

Mechanically speaking, the automated synthesizer may be roughly divided into three subsystems: the reaction vessel bank, the parent vessel, and the pressurized delivery system. As mentioned above, coupling synthesis takes place at the reaction vessel bank inside the reaction vessels. The parent vessel holds, pools and mixes the beads from all reaction vessels. The delivery system ensures that the proper solvent and/or reagent solution in an appropriate reagent/solvent concentration is delivered to either the parent vessel or the reaction vessel bank at an appropriate step in the synthesis process. Furthermore, the entire system is sealed during operation. Pressurization, where necessary, is done with an inert gas such as argon. Argon is the preferred pressurizing agent because of its availability and low chemical reactivity.

For ease of discussion, the automated synthesizer will now be described with reference to a specific example. The specific example used throughout this disclosure involves the synthesis on beads of a set of polypeptides. The beads are tagged for identification following each amino acid coupling reaction with four nucleotide monomers: A, T, C, and G.

It must be recognized, however, that the automated synthesizer is neither limited to the synthesis of the particular polymer described in the above specific example nor to tagged polymer synthesis. Although reference will be made throughout this disclosure to the synthesis of polypeptides and the tagging of beads with the above nucleotides utilizing a reaction vessel bank having nine reaction vessels, there is no inherent upper or lower limit in the number of reaction vessels which may be included in each reaction vessel bank. In fact, modular construction of the device permits easy addition of additional reaction vessel banks. Further, many other molecules and tags may be synthesized on the beads, or the tags may be eliminated entirely.

2.1 The Pressurized Delivery System

The detailed description of a pressurized delivery system 265, which has been specifically tailored to synthesize the polypeptides according to the specific example, has been divided into three parts: reservoirs for use synthesizing polypeptides, reservoirs for use in tagging beads, and the delivery valves.

2.2.1 Reservoirs for Use in Synthesizing Polypeptides

In addition to the nine amino acid monomers used to synthesize the peptides of the specific example, several other additional "common" reagents will be employed in the synthesis. In a typical peptide synthesis, for example, the following reagents may be employed:

TABLE 1

| Function | Chemical |
| --- | --- |
| Deprotection | 10% Piperidine in DMF |
| Activation | 0.2 M HBTU and 0.6 M DIEA in DMF/DCM mixture having a 3:1 ratio |
| Capping | acetic anhydride in THF<br>n-methyl imidazole in THF |
| Washing | DMF<br>THF |

2.2.2 Reservoirs for Use in Tagging Beads

In the specific example, the beads are optionally tagged. In a peptide synthesis reaction, the beads are in one embodiment tagged with a nucleic acid comprising nucleotides from the group A, T, C, and G. In addition to the four nucleotide reagents, the following solvents and reagents are used during the synthesis of tags.

TABLE 2

| Function | Chemical |
| --- | --- |
| Deprotection | trichloroacetic acid in DCM |
| Oxidation | $I_2$, collidine, $H_2O$, and MeCN |
| Activation | 0.5 M tetrazole in MeCn |
| Capping | acetic anhydride in THF<br>n-methyl imidazole in THF |
| Washing | MeCN |

These nucleotide reagents are contained in reservoirs having sufficient volume and quantity to accomplish the synthesis of tags utilizing the automated synthesizer.

Figure 2:
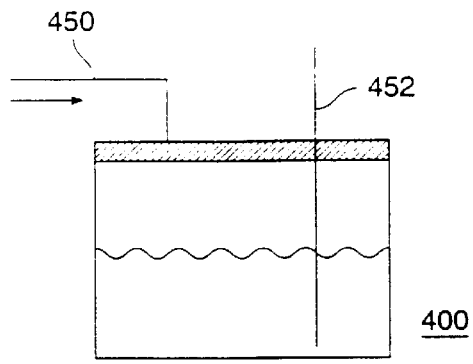
FIG. 2 shows a schematic diagram of a reagent reservoir.

FIG. 2 shows a representative reservoir 400 for containing, for example, the MeCN solution in Table 2. There are two tubes associated with each reservoir listed in Tables 1 and 2. As shown in FIG. 2, a tube 450 contains pressurized argon for pressurizing the reservoir to force the contents of the reservoir up a second tube 452. In some embodiments, the reagent reservoirs are always pressurized. In other embodiments, the argon tube is controlled by a local on/off valve to pressurize a reagent reservoir only when the contents of that reservoir are needed.

2.2.3 Delivery Valves

Figure 3:
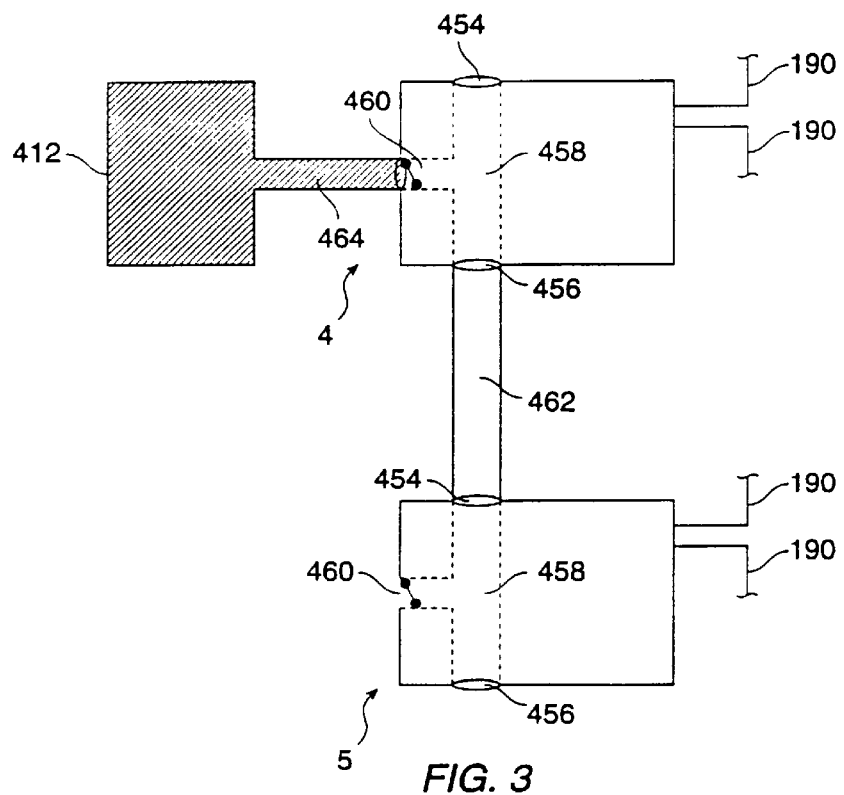
FIG. 3 shows a 3-port valve used in the synthesizer.

FIG. 3 shows a representative 3-port solenoid valve in greater detail. The valve may be, for example, a Model 2-110–900 by General Valve Corp. of Fairfield, N.J. Further, the 3-port valve of FIG. 3 represents, for example, valve 4 which delivers a reagent from reservoir 412. Three-port valves are used in the pressurized delivery system 265 of FIG. 1. The 3-port solenoid valve employed in the present embodiment includes a first port 454 and a second port 456. The 3-port solenoid valve also has a channel 458 through its body that communicates with first port 454 and second port 456 and always permits a fluid to flow freely between the first and second port. To form a common manifold 462, second port 456 is coupled with, for example, first port 454 of another 3-port valve. The other 3-port valve may be, for example, valve 5 of FIG. 1. A solenoid inside the valve, responsive to a control signal through wires 190, selectively permits a third port 460 to communicate with channel 458. Third port 460 of valve 4 is coupled to reservoir 412 of FIG. 1.

To control the injection of a reagent from reservoir 412 into manifold 462 a line 464 carrying the pressurized reagent is connected to third port 460 of valve 4. At an appropriate moment, the solenoid opens and permits third port 460 to communicate with channel 458, thereby causing the pressurized reagent from third port 460 to be injected into channel 458 of valve 4 and into common manifold 462.

Figure 4:
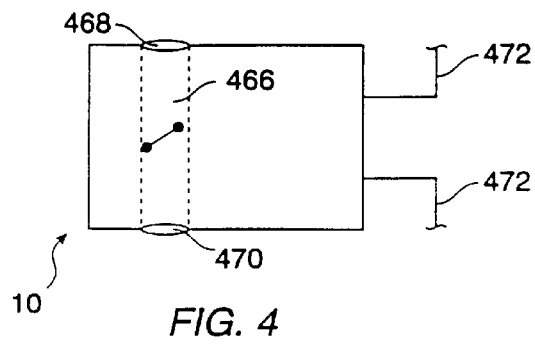
FIG. 4 shows a 2-port valve used in the synthesizer.

FIG. 4 shows a representative on/off 2-port solenoid valve 10. This valve may be, for example, a Model 2-17-900 by General Valve Corp. of Fairfield, N.J., for selectively permitting a fluid or a gas to flow in a channel between its two ports. As shown in FIG. 4, valve 10 includes two ports 468 and 470. Valve 10 also has a channel through its body that communicates between a first port 468 and a second port 470 to permit a fluid or a gas to flow between the two ports. A solenoid inside valve 10, responsive to a control signal through wires 472, selectively permits first port 468 to communicate with second port 470. When one port of valve 10 is connected to a tube carrying a pressurized gas or fluid, valve 10 can be used to permit or inhibit flow from that port to the other port of valve 10.

Figure 5:
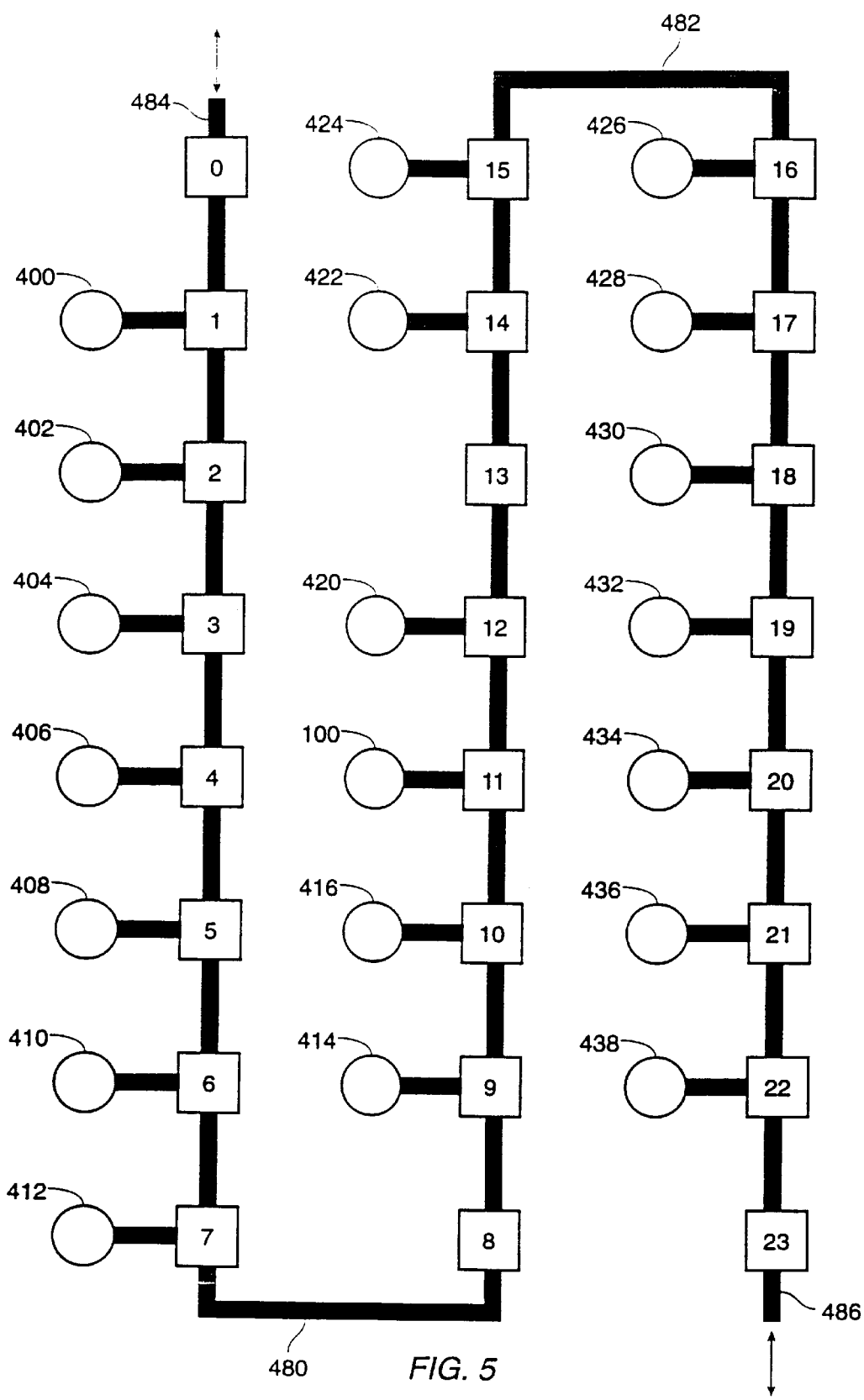
FIG. 5 shows a pressurized delivery system according to one aspect of the present invention.

FIG. 5 shows in greater detail a pressurized delivery system 265 according to one aspect of the present invention. FIG. 5 shows 24 valves 0–23 through which a common manifold is formed. The 2-port and 3-port valves are daisy-chained by coupling their first and second ports together so as to form a common manifold through which reagent flows. Three-port valves 1–7, 9–12, and 14–22 may be, for example, substantially similar to valve 4 of FIG. 3. Two-port valves 0, 8, 13, 23 may be, for example, substantially similar to valve 10 of FIG. 4. The common manifold includes the through channels of the 3-port valves and of the on/off valves, as well as the coupling tubes between adjacent valves. As previously mentioned, the third port of a 3-port valve is controlled by a solenoid in the valve. The third port of each 3-port valve is coupled to a tube from a reagent or solvent reservoir to transfer a reagent or solvent to and from PDS 265. Alternatively, the third port of a 3-port valve may serve as an exit port for delivering reagents to, for example, valve 100 of a reaction vessel bank. Two-port valves are used primarily as isolation valves or argon supply valves.

As shown in FIG. 5, the 24 valves are physically arranged in three separate banks to save space. The delivery system of FIG. 5 also includes a tube 480 for connecting the left bank of valves with the center bank. A tube 482 connects the right bank with the center bank. Table 3 lists the valves used in the delivery system, specifying the types of valves used and the reagent reservoir controlled by each valve in a typical embodiment.

TABLE 3

| Valve | Type | Reservoir | Reservoir Content |
|---|---|---|---|
| 0 | On/Off | —) | Argon |
| 1 | FWO 60 | 400 | MeCN |
| 2 | FWO 60 | 402 | 1% trichloroacetic acid in DCM |
| 3 | FWO 60 | 404 | Tetrazole |
| 4 | FWO 30 | 406 | C |
| 5 | FWO 30 | 408 | T |
| 6 | FWO 30 | 410 | G |
| 7 | FWO 30 | 412 | A |
| 8 | On/Off | — | — |
| 9 | FWO 30 | 414 | Waste |
| 10 | FWO 30 | 416 | Bottom of Parent Vessel |
| 11 | FWO 30 | 100 | RV Banks |
| 12 | FWO 30 | 420 | Waste |
| 13 | On/Off | — | — |
| 14 | FWO 60 | 422 | Top Parent |
| 15 | FWO 60 | 424 | $I_2$, collidine, $H_2O$, MeCN |
| 16 | FWO 60 | 426 | Acetic anhydride in THF |
| 17 | FWO 60 | 428 | n-methyl imidazole in THF |
| 18 | FWO 60 | 430 | Piperidine |
| 19 | FWO 60 | 432 | HBTU |
| 20 | FWO 60 | 434 | DIEA |
| 21 | FWO 60 | 436 | MeCN |
| 22 | FWO 60 | 438 | DMF |
| 23 | On/Off | — | Argon |

For example, valve 22 is shown to be a FWO60 valve or a fast wash out (FWO) 3-port valve having a $60/1000$-inch through channel. Furthermore, valve 22 controls a reagent from pressurized reservoir 438 which, as indicated by Table 3, contains DMF. As a further example, valve 22 is an on/off valve controlling the flow of pressurized argon from an argon supply source (not shown) to the common manifold of PDS 265.

FIG. 5 shows a tube 484 connected to valve 0 for pressurizing the common manifold of PDS 265 from one end. Another tube 486 is connected to valve 23 and pressurizes the common manifold of PDS 265 with argon from the other end.

As an illustration, the operation of pressurized delivery system 265 during a peptide synthesis deprotection cycle is described below. For deprotection of polypeptides, a solution of 10% piperidine in DMF is delivered to the reaction vessels in the reaction vessel (RV) bank. Table 3 indicates that valve 18 permits the flow of piperidine from reservoir 430. Consequently, valve 18 needs to open to permit piperidine from pressurized reservoir 430 to flow into the common manifold of PDS 265. To force the solution to enter RV bank valve 11, isolation valve 8 is closed and isolation valve 13 opens to force the pressurized piperidine to enter open RV bank valve 11.

As shown in FIG. 5 and Table 3, RV bank valve 11 and parent vessel valve 10 are centrally located in the chain of valves. This arrangement advantageously minimizes the length of the manifold section between these valves and a given reagent valve. Consequently, a smaller volume of reagent is required to fill up this manifold section. Isolation valves 8 and 13 can be closed to prevent the reagent from one end of the manifold from overshooting RV bank valve 11 or parent vessel valve 10 and from unnecessarily entering another portion of the common manifold.

Table 3 also shows valves 4–7 and 9–12 to be 3-port valves having a through channel dimension of $30/1000$ inch. In contrast, the remaining valves in the manifold have a through channel dimension of $60/1000$ inch. The reduced channel cross section further reduces the volume in the respective portion of the manifold. Consequently, less reagent is needed to fill up the manifold.

For example, nucleotides A, T, C, and G are relatively costly. It is therefore desirable to keep the volume of reagent used to the necessary minimum. Nucleotide valves 4–7 are located proximate to RV bank exit valve 11 to keep the distance between a nucleotide valve and RV bank exit valve 11 short and the required volume of reagent low. The cross section of the manifold along the path from any nucleotide valve to RV bank exit valve 11 is also kept small to further reduce the volume of nucleotide reagent present in the manifold. In fact, tube 480 of FIG. 5 as well as the portion of the manifold between the nucleotide valves and isolation valve 8 have a reduced cross section of $30/1000$ inch.

3. Reaction Vessel Banks

Figure 6:
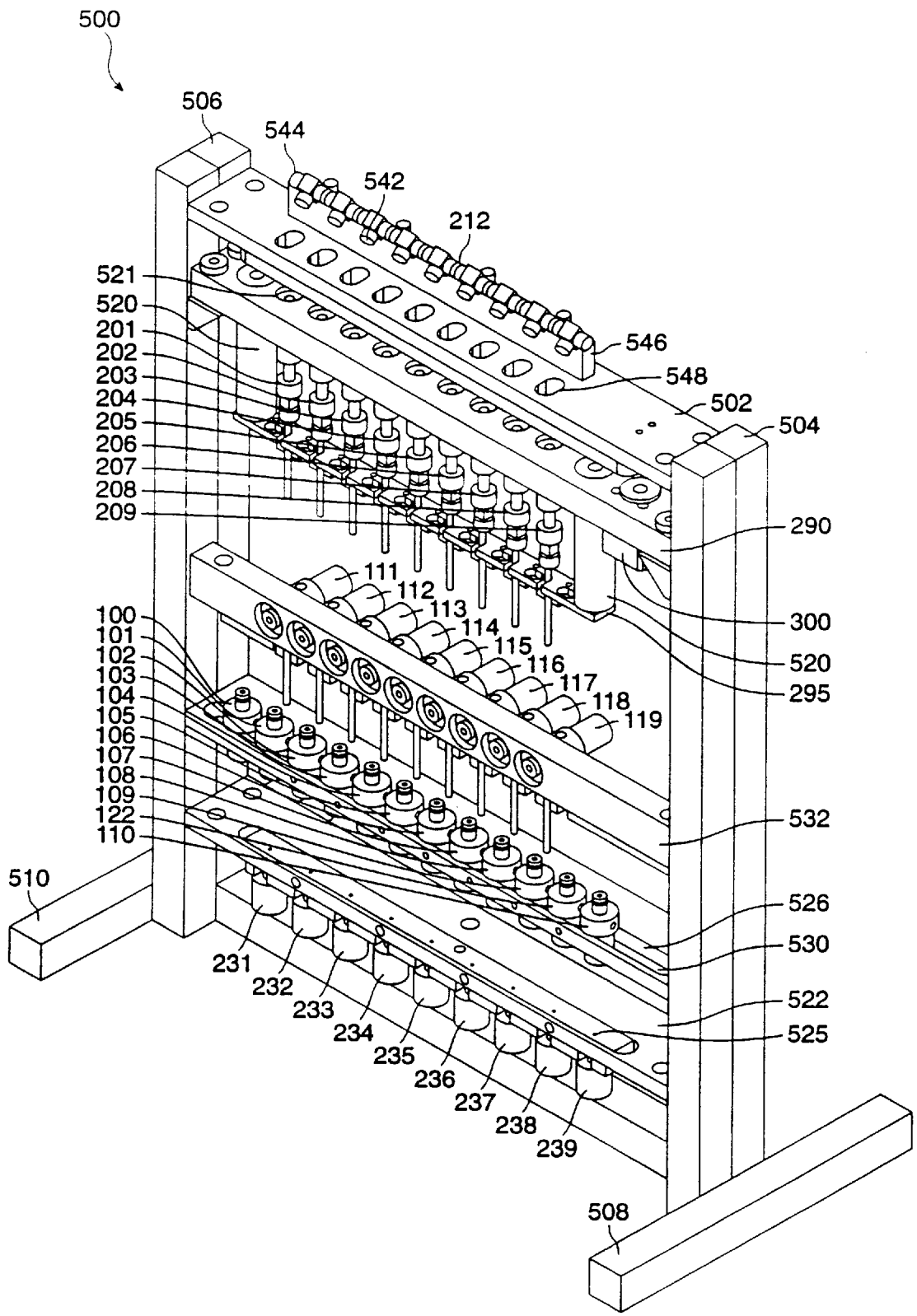
FIG. 6 shows a reaction vessel bank.

FIG. 6 shows a simplified reaction vessel bank 500 according to one aspect of the present invention. For ease of illustration, tubes through which solution flows have been partially deleted. Reaction vessel bank 500 includes a top bracket 502, two side brackets 504 and 506, and two bases 508 and 510. A top reaction vessel bracket 290 attaches to side brackets 504 and 506. A vortexing motor 300 attaches to top reaction vessel bracket 290 for supplying an agitation force to a plurality of reaction vessels 201–209 via a drive belt 521. The bottom of reaction vessels 201–209 are attached to a bottom reaction vessel bracket 295. Brackets 502, 504, 506, 290, and bases 508 and 510 may be constructed from any suitable material. For ease of machining, strength, and light weight, aluminum is used to construct the above-mentioned brackets in the present embodiment.

Bottom reaction vessel bracket 295 is attached to top reaction vessel bracket 290 by two nonconcentric shafts 280 inside shaft housings 520. Nonconcentric shafts 280 are rotatably mounted through apertures (not shown) in top reaction vessel bracket 290. Nonconcentric shafts 280 are operatively coupled to a vortexing motor 300 through belt 521. As will be discussed later, nonconcentric shafts 280 translate the rotational force supplied by vortexing motor 300 to an agitation force for urging bottom reaction vessel bracket 295 to move in a circular pattern. This circular motion exerts a vortexing effect upon the contents of reaction vessels 201–209. Because every reaction vessel 201–209 is attached at its respective lower end to bottom reaction vessel bracket 295, all reaction vessels are agitated uniformly and simultaneously.

FIG. 6 also shows a bottom bracket 522. Bottom bracket 522 is attached to side brackets 504 and 506 and may also be constructed from any suitable material, including aluminum. A plurality of amino acid reservoirs 231–239 are mounted beneath bottom bracket 522. The amino acid reagents in amino acid reservoirs 231–239 are used as building blocks for synthesizing the set of polypeptides of the specific example. The present embodiment contemplates using nine different amino acid monomers per bank for synthesizing the set of polypeptides.

FIG. 6 also shows an isolation valve bracket 526 attached to side brackets 504 and 506. Isolation valve bracket 526 includes a channel 530 for mounting a plurality of lower manifold valves 101–109. As shown in FIG. 6, each lower manifold valve 101–109 is secured within channel 530 in the present embodiment. However, lower manifold valves 101–109 may be secured to isolation bracket 526 using commercially available mounting hardware or other mounting methods. Lower manifold valves 101–109 are 3-port solenoid valves and are the same as the 3-port valve discussed earlier in connection with FIG. 3. As used in reaction vessel bank 500, the through channels of lower manifold valves 101–109 are coupled together to form a common lower manifold 214 through which solution from the pressurized delivery system 265 flows.

Three 2-port valves 100, 110, and 122 are also shown in FIG. 6. Nine valves 101–109 control the flow of solution from lower manifold 214 to the nine reaction vessels 201–209. Isolation valve 110 at a first end of the common lower manifold 214 opens to a waste line (not shown in FIG. 6). Isolation valve 100 at a second end of common lower manifold 214 selectively inhibits or permits the flow of solution from PDS 265 to the rest of the common lower manifold 214. An optional isolation valve 122 supplies local argon pressure to assist in the delivery of solution to and from various portions of reaction vessel bank 500.

In another embodiment, the eleven isolation valves 100–110 and 122 are provided for in an 11-valve block such as model P/N601374, by ABI of Foster City, Calif. The block comes preassembled and thus simplifies construction. The eleven valves of the 11-valve block function substantially as discussed above.

An injection valve bracket 532 made of a suitable material such as aluminum is attached to side brackets 504 and 506. A plurality of injection valves 111–119 are mounted through apertures in injection valve bracket 532. FIG. 6 shows a total of 9 injection valves 111–119 to control the injection of amino acids from nine amino acid reservoirs 231–239. Injection valves 111–119 are 3-port solenoid valves and are the same as the 3-port valve discussed earlier in connection with FIG. 3. The first port of each injection valve couples to a reaction vessel 201–209 while the second port of each injection valve is coupled to the third port of a lower manifold valve 101–109. The coupling is accomplished with appropriately sized tubes, such as the ¹⁄₁₆-inch teflon tubes employed in the present embodiment. As is apparent from the foregoing, the through channel of each injection valve 111–119 permits a solution to flow freely between a reaction vessel 201–209 and the third port of a lower manifold valve 101–109. The third port of each injection valve 111–119 is connected to an amino acid reservoir 231–239 to selectively inhibit or permit an amino acid to be injected into a stream of solution flowing between a lower manifold valve 101–109 and a reaction vessel 201–209.

FIG. 6 also shows a top common manifold 212. Top common manifold 212 includes nine manifold ports 542 for connecting top common manifold 212 to the nine reaction vessels 201–209. In the present embodiment, ⅛-inch flexible teflon tubes are used to couple manifold ports 542 to the top end of reaction vessels 201–209. Top common manifold 212 also includes a first end port 544 for connecting with a parent vessel (not shown in FIG. 6) where the beads from individual reaction vessels 201–209 are pooled and mixed together. A second end port 546 connects top common manifold 212 with a 3-port pressure/vent valve (not shown in FIG. 6). The pressure/vent valve and second end port 546 provide another route through which pressurized argon, solutions, reagents, etc., may be supplied to top common manifold 212. Alternatively, the pressure/vent valve and second end port 546 provide an additional route through which pressurized argon, solutions, etc., may be vented from top common manifold 212 to the appropriate reservoir.

Figure 7:
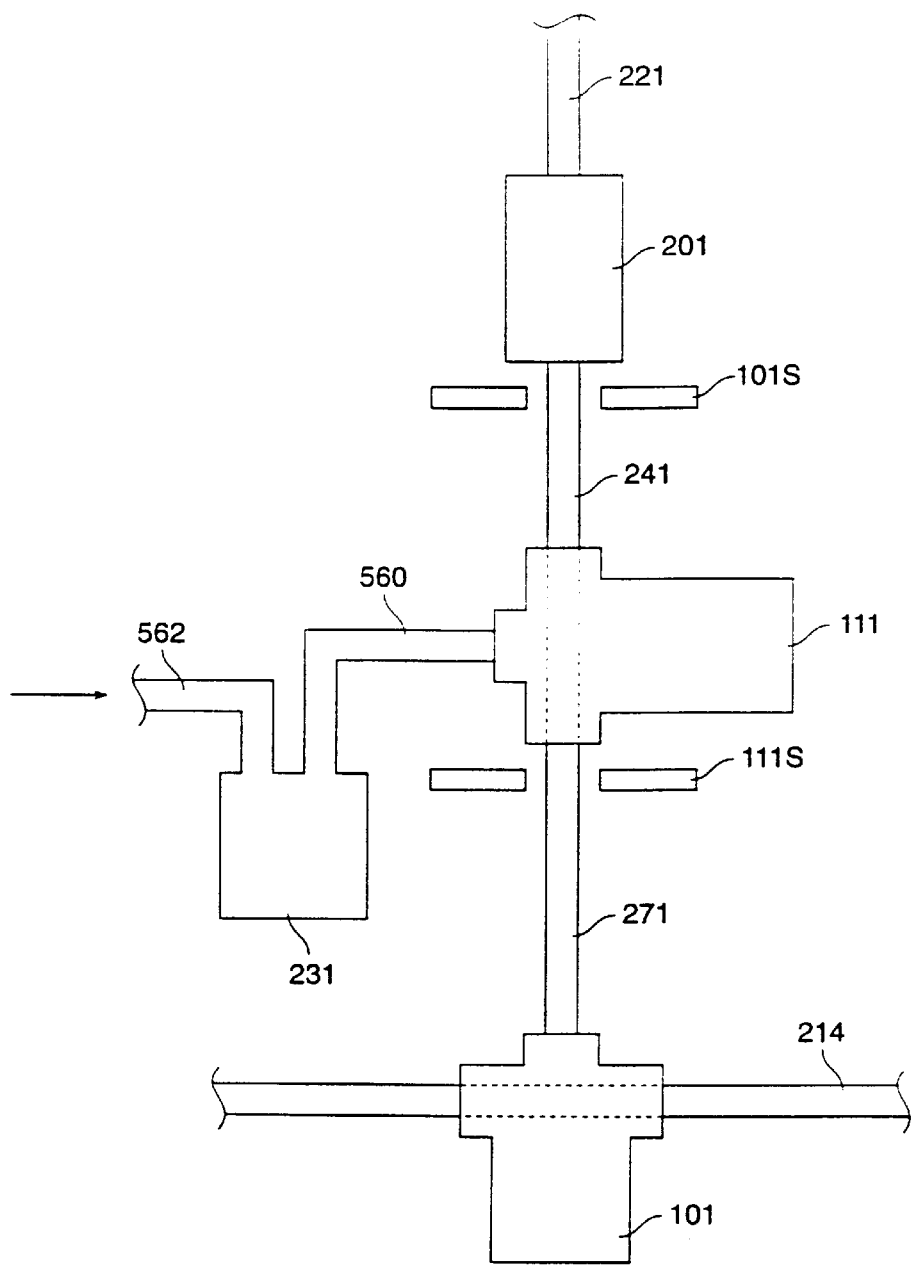
FIG. 7 shows the interconnections among a lower manifold valve, an injection valve, a reagent reservoir, and a reaction vessel.

FIG. 7 shows in greater detail the interconnections among an amino acid reservoir 231–239, an injection valve 111–119, a lower manifold valve 101–109, and a reaction vessel 201–209. A lower manifold valve, for example, valve 101, which is a three-port valve, is connected to common lower manifold 214 so as to permit a solution to flow freely between the first port and the second port of lower manifold valve 101. The third port of lower manifold valve 101 is connected via tube 271 to either the first or second port of the 3-port injection valve 111. The other port of either the first or second port is connected to one end of reaction vessel 201 via tube 241. The other end of reaction vessel 201 is connected to a manifold port 542 of top common manifold 212 (not shown in FIG. 7) via a tube 221. Tubes 271, 241, and 221 are made from a chemically resistant material such as teflon. In fact, the present embodiment employs translucent PTFE and FEP teflon tubes of various cross-sectional dimensions throughout because of the low reactivity and optical characteristics of the translucent teflon material.

Amino acid reservoir 231 is pressurized with an inert gas such as argon via tube 562. The pressurized amino acid solution in amino acid reservoir 231 enters the third port of 3-port injection valve 111 through tube 560. Upon receipt of an appropriate command, injection valve 111 opens to permit the pressurized amino acid solution to enter the through channel of injection valve 111.

FIG. 7 also shows two optical sensors 111S and 101S. Optical sensors 111S and 101S detect the presence or absence of a liquid within substantially translucent teflon tubes 271 and 241. As shown in FIG. 7, optical sensor 111S is positioned below injection valve 111 and optical sensor 101S is positioned below reaction vessel 201. Data from optical sensors 111S and 101S are sent to a control computer (not shown in FIG. 7) for use in controlling various phases of the synthesis reaction.

Figure 8:
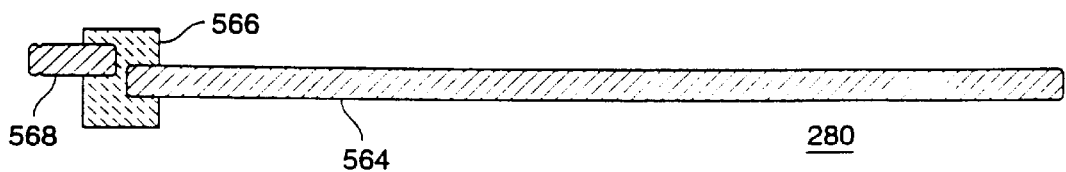
FIG. 8 shows a nonconcentric agitator.

FIG. 8 shows in greater detail the nonconcentric agitator 280 of FIG. 1. Nonconcentric agitator 280 includes two cylindrical shafts 564 and 568 coupled to a cylindrical knuckle 566. Shaft 564 aligns longitudinally with the radial axis of cylindrical knuckle 566 and is coupled at one of the two planar surfaces of cylindrical knuckle 566. Shaft 568 is coupled to the other planar surface of cylindrical knuckle 566 and is offset from the radial axis of cylindrical knuckle 566. In one embodiment, shafts 564 and 568, and cylindrical knuckle 566 are machined from a single piece of metal stock.

When cylindrical shaft 564 is torqued to rotate within a fixed rotary support such as a roller bearing, cylindrical shaft 568, which is offset from the axis of rotation of cylindrical shaft 564, moves in a circular path around the axis of rotation of cylindrical shaft 564. More than one nonconcentric agitator 280 may be operatively coupled, for example, by a belt-and-pulley arrangement to allow a plurality of nonconcentric agitators 280 to move in unison. In the present embodiment, shafts 568 of two nonconcentric agitators 280 are connected to a single bracket to move the bracket in a circular path when shafts 564 are rotated. Furthermore, shafts 568 and vortexing motor 300 are designed to move the bottom of each reaction vessel in a circular path at approximately 1500 revolutions per minute. To prevent damage to beads, the circular path of the present embodiment is preferably limited to a radius of approximately 3.5 mm.

Figure 9:
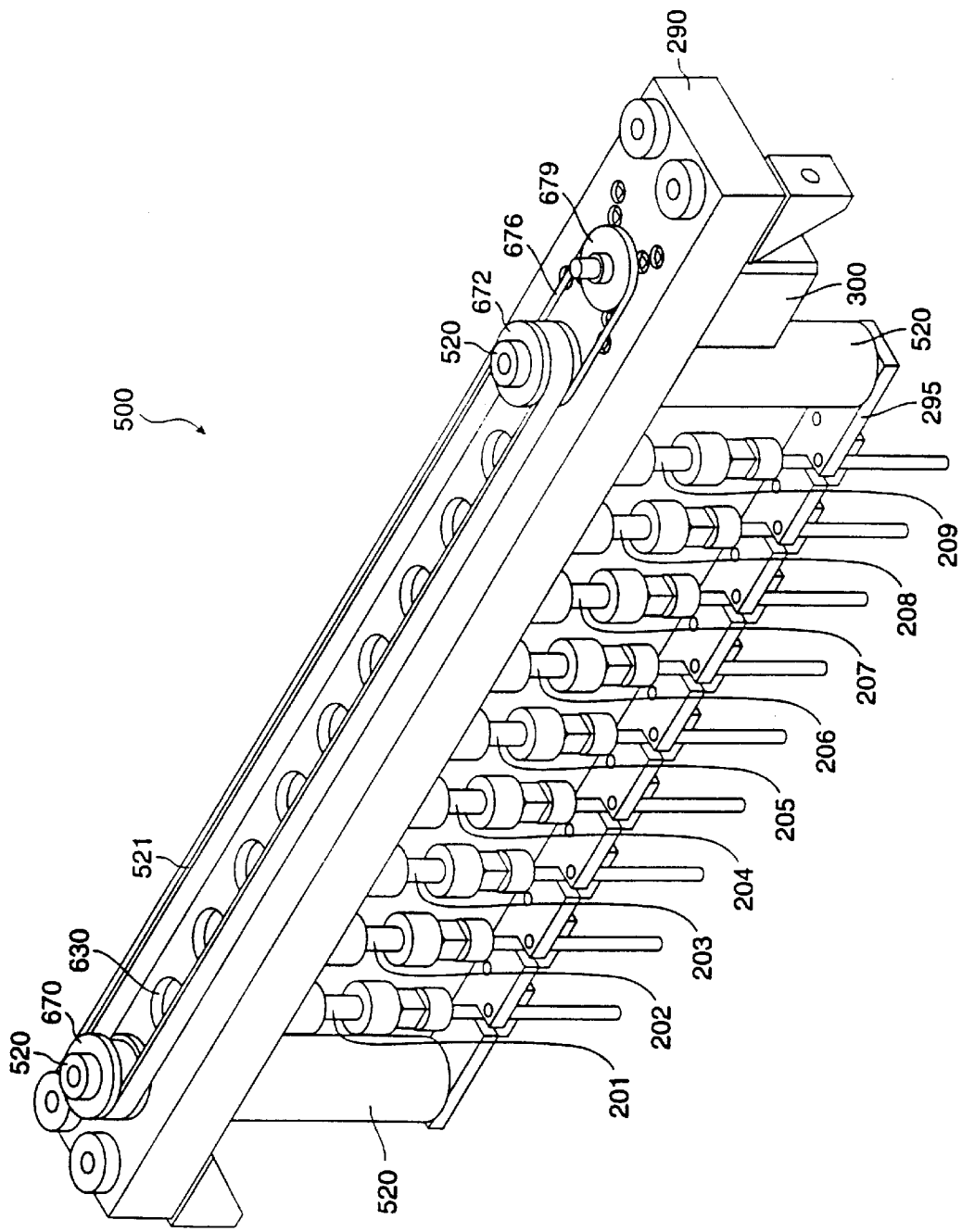
FIG. 9 shows the upper portion of a reaction vessel bank.

FIG. 9 shows in greater detail the upper portion of the reaction vessel bank 500 including reaction vessels 201–209 and vortexing motor 300 of FIG. 6. As discussed in connection with FIG. 6, reaction vessel bank 500 includes a plurality of reaction vessels 201–209 connected to top bracket 290. Top bracket 290 has a plurality of apertures 630 at which reaction vessels 201–209 connect. A teflon tube from above the aperture (not shown) connects to the upper end of each reaction vessel 201–209 at aperture 630 in a manner that permits a fluid to flow freely between the teflon tube and reaction tube 201–209.

Figure 10A:
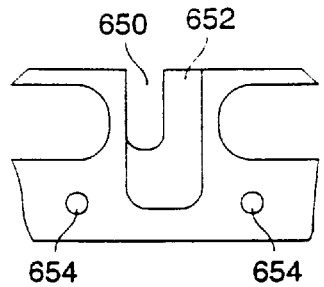
FIGS. 10A and 10B show a lower reaction vessel bracket.
Figure 10B:
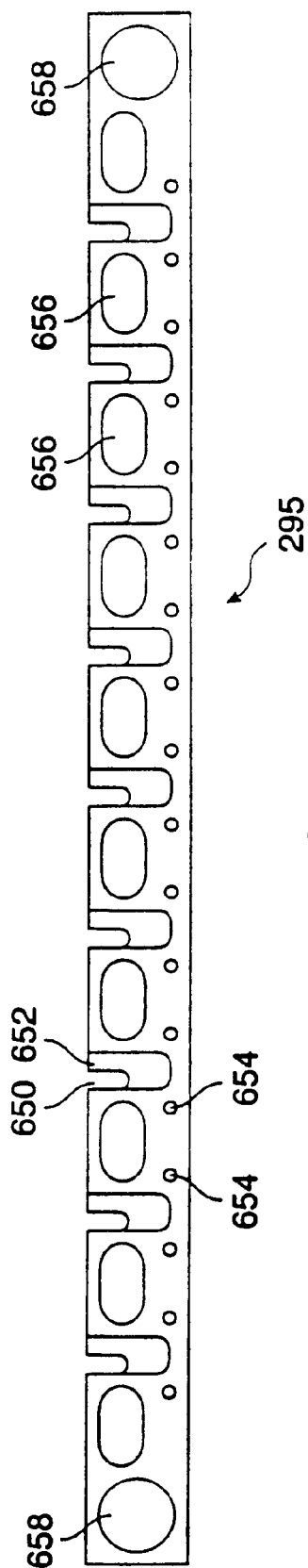

The lower ends of reaction vessels 201–209 are connected to lower reaction vessel bracket 295. FIGS. 10A and 10B show in greater detail a bottom view of the lower reaction vessel bracket 295 of FIG. 6. FIG. 10A is a close-up bottom view of a portion of lower reaction vessel bracket 295.

FIG. 10B shows a plurality of channels 650 in lower reaction vessel bracket 295. A flexible and substantially translucent teflon tube (omitted from FIG. 10B for ease of illustration) extends from the lower end of each reaction vessel 201–209 (also omitted from FIG. 10B for ease of illustration) and fits in a channel 650. A groove 652 for mounting an optical sensor is associated with each channel 650. Groove 652 is clearly illustrated in FIG. 10A.

FIG. 10B shows a plurality of mounting holes 654 for securely fastening optical sensors to lower reaction vessel bracket 295. Also shown in FIG. 10B is a plurality of optional holes 656 for reducing weight. As discussed earlier, lower reaction vessel bracket 295 follows the motion of the nonconcentric agitators in a circular path to vortex the contents of the reaction vessels. Optional holes 656 may be machined through lower reaction vessel bracket 295 to reduce the mass of the bracket, thereby reducing the amount of power needed to move the bracket.

A through hole 658 near each end of lower reaction vessel bracket 295 connects a nonconcentric agitator 280 to lower reaction vessel bracket 295. The lower ends of reaction vessels 201–209, which are extended by flexible teflon tubes 241–249 to fit through channels 650 in lower reaction vessel bracket 295, follow the circular movement of lower reaction vessel bracket 295. As lower reaction vessel bracket 295 moves in a circular path, the contents of all reaction vessels 201–209 in a reaction vessel bank are vortexed in a parallel manner.

FIG. 9 also shows optional nonconcentric agitator housings 520 for fitting over nonconcentric agitators 280. Optional nonconcentric agitator housings 520 enclose the nonconcentric shafts within a hollow cylindrical housing to prevent possible injury to human users and damage to equipment when the nonconcentric shafts are in motion.

The present embodiment uses a stepper motor (Model PX245-01AA by Oriental Motor U.S.A. Corp. of Torrance, Calif.) along with a stepping motor controller (Model RD122 by Semix Corp., of Fremont, Calif.) for supplying the rotational force to the nonconcentric agitators. As shown in FIG. 9, three pulleys 670, 672, and 674 cooperate with vortexing motor 300 and two drive belts 521 and 676 to rotate the two nonconcentric agitators 280 in unison inside optional nonconcentric agitator housings 520. Although the present embodiment utilizes a stepper motor and a stepping motor controller, the rotational force may be supplied by any other suitable type of motors, including other electrical or pneumatic motors. Furthermore, the force supplied by vortexing motor 300 may be transmitted to nonconcentric agitators 280 by any suitable transmission means including chains and sprockets, pulleys and belts, gears, etc.

Figure 11A:
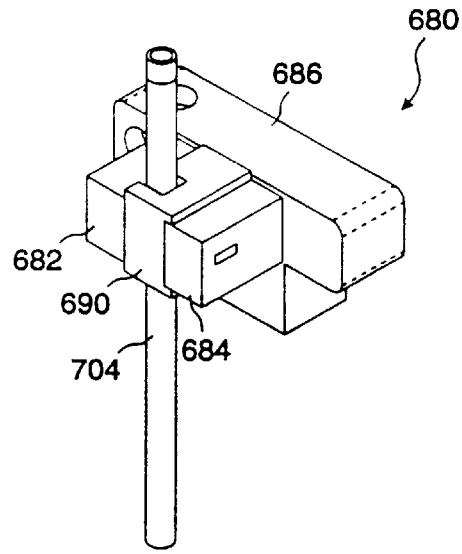
FIG. 11A–11D show an optical alignment block for use with optical sensors to detect the presence of a liquid within a substantially translucent tube according to one aspect of the present invention.

FIG. 11A shows a representative optical sensor 680 for use in detecting the presence or absence of a fluid within a substantially translucent teflon tube. Optical sensor 680 is the same as optical sensors 101S–119S of the present embodiment. Optical sensor 680 (Model EE-SX671 by Omron, Inc. of Schaumburg, Ill.) includes two forked ends 682 and 684 for housing a light transmitter and a collector, respectively. Optical sensor 680 also has a body 686 for housing the appropriate electronic circuitry to transmit sensor data to a control computer and for attaching optical sensor 680 to a bracket.

Figure 11B:
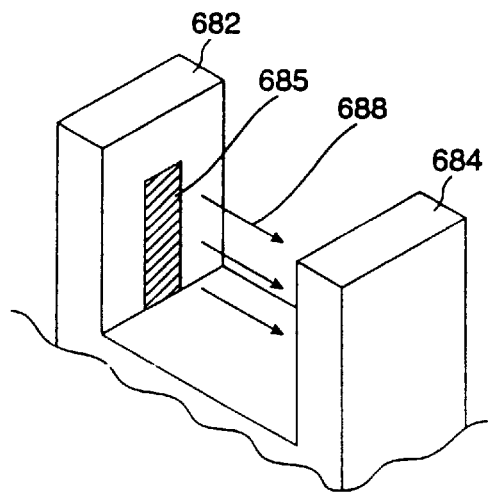

FIG. 11B shows in greater detail forked ends 682 and 684 of optical sensor 680. Located at the interior surface of forked end 682 is a substantially rectangular transmitter 685 for transmitting light to a substantially rectangular collector (not shown in FIG. 11B) in the direction of arrows 688. The collector is located at the interior surface of forked end 684 and is likewise of a substantially rectangular shape. To detect the presence of a fluid within a substantially translucent teflon tube, the teflon tube is fitted through the gap between the two forked ends 682 and 684. When a fluid is present within the substantially translucent teflon tube, the collector is triggered signifying detection of a fluid within the teflon tube.

Figure 11C:
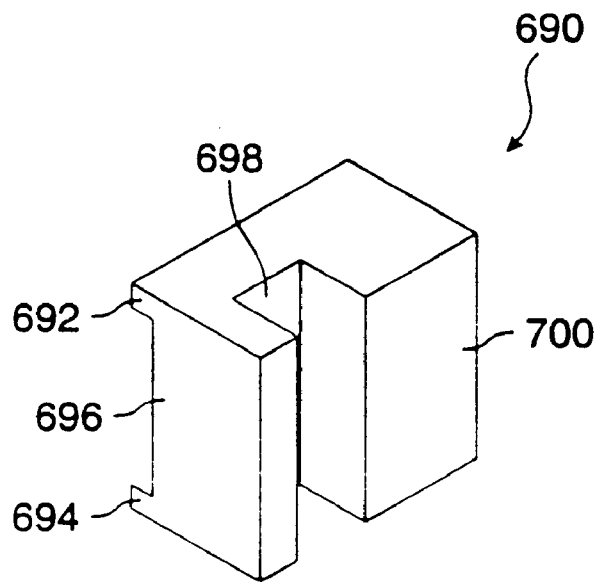

In practice, it was discovered that the substantially translucent teflon material may, when empty, cause optical sensor 680 to fail to trigger. To advantageously use common optical sensors to sense the presence of a liquid inside a substantially translucent tube, a novel optical alignment block is used. FIG. 11C shows in greater detail an optical alignment block 690. Optical alignment block 690 is made of an opaque material which substantially blocks any light emitted by transmitter 685. Optical alignment block 690 includes two retaining walls 692 and 694 at a first surface 696 for frictionally engaging block 690 with one of the forked ends of optical sensor 680, and to securely hold optical alignment block 690 between the forked ends. In one embodiment, retaining walls 692 and 694 are designed to engage the collector forked end 684 of FIG. 11B.

Optical alignment block 690 also includes a channel 698 built into a second block surface 700. Second block surface 700 is the surface opposite the above-mentioned first surface 696. The axis of channel 698 is orthogonal to retaining wall 692 and 694. Channel 698 is sized to grip the teflon tube snugly. As a result, the teflon tube is secured within channel 698 and is aligned at a right angle with respect to the above-mentioned transmitter strip 685 when optical alignment block 700 is fitted into the gap between forked ends 682 and 684.

Figure 11D:
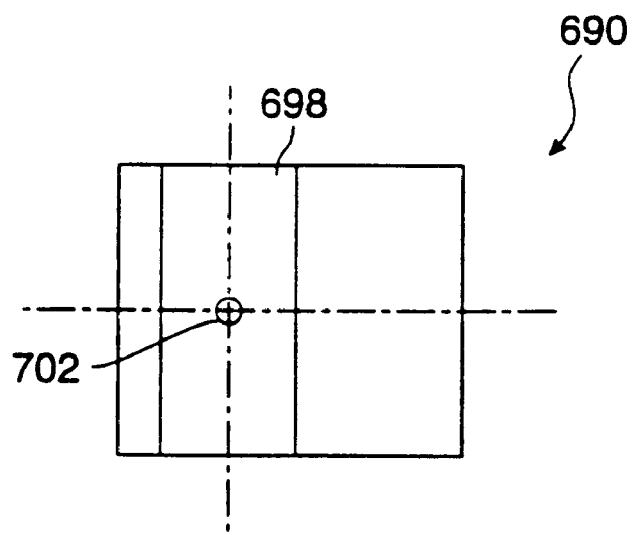

FIG. 11D shows an aperture 702 located along the center line of channel 698. Aperture 702 permits a small amount of light to travel through optical alignment block 690 along its bore between first surface 696 and second surface 700.

When a substantially translucent teflon tube such as tubes 241–249 or 271–279 is fitted snugly within channel 698, the axis of aperture 702 runs through the center of the teflon tube. The shape and size of aperture 702 is a function of the optical properties of the tubes.

When optical alignment block 690 is fitted between forked ends 682 and 684 in the manner shown in FIG. 11A, light from transmitter 685 in forked end 682 travels through a substantially translucent tube 704. Most of the light is blocked by optical alignment block 690 after passing through tube 704. Some of the light passing through tube 704 reaches aperture 702 (hidden from view in FIG. 11A) and travels along the bore of aperture 702 to reach the collector within forked end 684.

Since the axis of aperture 702 runs through the center of substantially translucent tube 704, light passing through the center of the tube reaches a portion of the collector in forked end 684. Since light going through empty tube 704 is diffracted, an insufficient amount of light reaches the collector to trigger the sensor. When a fluid is present within translucent teflon tube 704, light passing through the filled tube is focused by the fluid within. The focused light enters aperture 702 from the direction of forked end 682 to trigger the collector in forked end 684. When a fluid is absent, the focusing effect is less pronounced. Consequently, less light enters aperture 702. In fact, when there is no fluid in teflon tube 704, there is insufficient light passing through aperture 702 to trigger the collector in forked end 684.

As discussed earlier, optical alignment block 690 is sized to snugly grip teflon tube 704. When optical alignment block 690 is fitted between forked ends 682 and 684, the teflon tube is securely gripped, as shown in FIG. 11A, by optical sensor 680 and block 690. By securing optical sensor 680 to a bracket, teflon tube 704 is thereby secured to the bracket. In this manner, the teflon tubes 241–249 extending from the bottom of reaction vessels 201–209 of this embodiment are secured to the bottom reaction vessel bracket 295.

Figure 12:
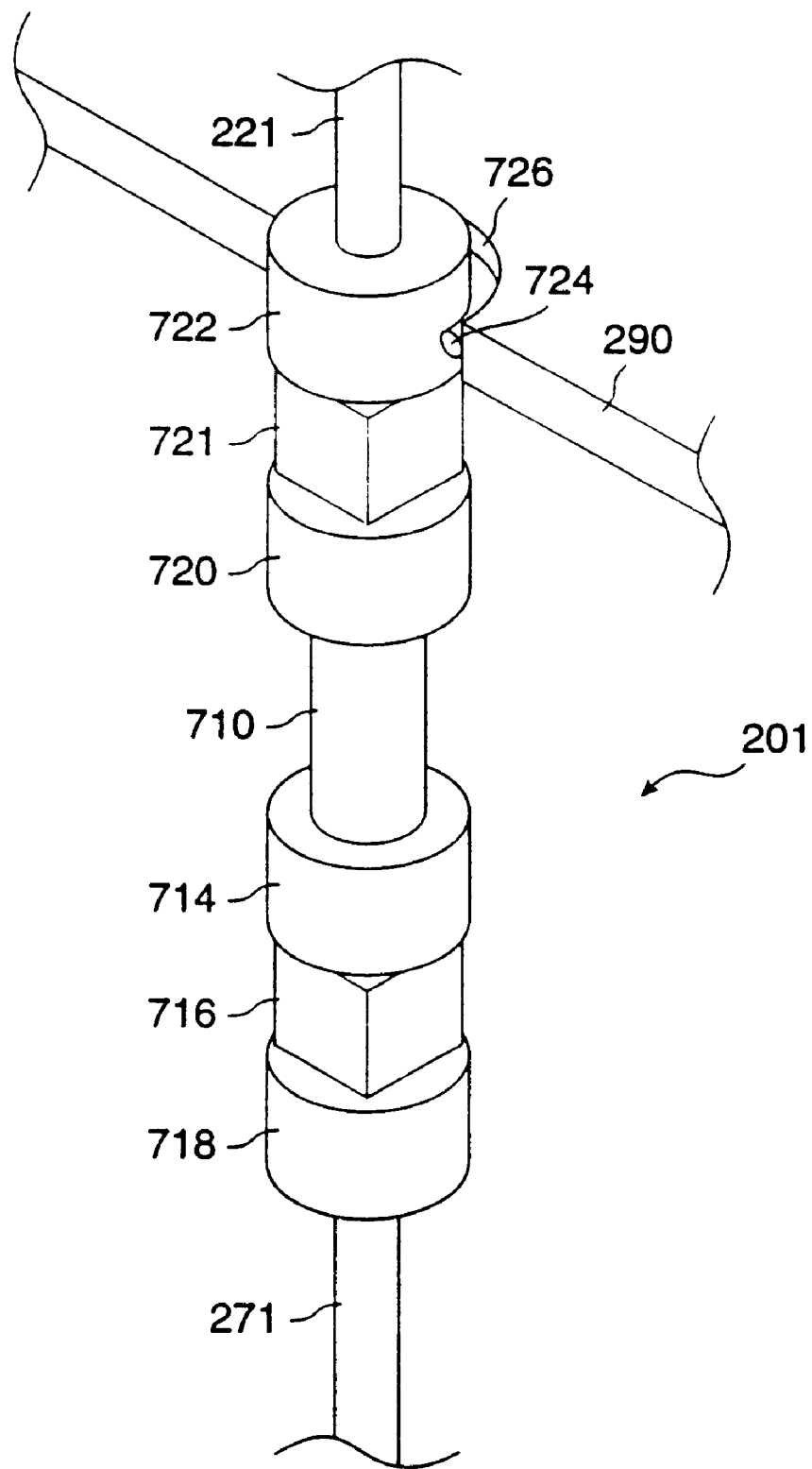
FIG. 12 shows a reaction vessel according to one aspect of the present invention.

As shown in FIG. 12, a reaction vessel such as reaction vessel 201 of the present embodiment consists of a segment of FEP teflon tube 710. Tube 710 has an outside diameter of ¼ inch and an inside diameter of 0.19 inch. Tube 710 is sealingly coupled with a flexible teflon tube 271. Flexible teflon tube 271 is secured to lower reaction vessel bracket 295 of the reaction vessel bank. As the lower reaction vessel bracket 295 moves in a circular motion, flexible teflon tube 271 follows the circular motion described by the bottom reaction vessel bracket 295 to vortex the contents within tube 710.

In this embodiment, tube 271 has an outside diameter of ⅛ inch and an inside diameter of 1/16 inch. FIG. 12 shows a tube connector comprising a first coupler 714, a second interconnector 716, and a third coupler 718 for sealingly connecting tubes of different cross-sectional dimensions together. The aforementioned tube connector is available from Norton, Inc. of Akron, Ohio. There is a frit or filter (hidden from view in FIG. 12) located at the bottom end of tube 710 for preventing substrates within tube 710 from entering flexible tube 712. The frit may be, for example, 2 micron titanium frit.

At the other end of tube 710, a fourth coupler 720, a fifth interconnector 721, and a sixth coupler 722 sealingly connect tube 710 to a tube 221. The couplers 720 and 722 as well as interconnector 721 are necessary because tube 221 of the present embodiment has different cross-sectional dimensions from tube 710. Tube 221 connects to a manifold port 542 of top manifold 212 (not shown in FIG. 6).

A flexible O-ring 724 is fitted within a hole 726 in bracket 290 (shown in FIG. 12 in a cutaway view). O-ring 724 flexibly grips coupler 722, thereby flexibly securing reaction vessel 201 to bracket 290. When the bottom end of reaction vessel 201 is agitated, O-ring 724 serves as a pivot point and holds the top end of reaction vessel 201 relatively immobile to enhance the vortex effects.

4. Parent Vessel

Figure 13:
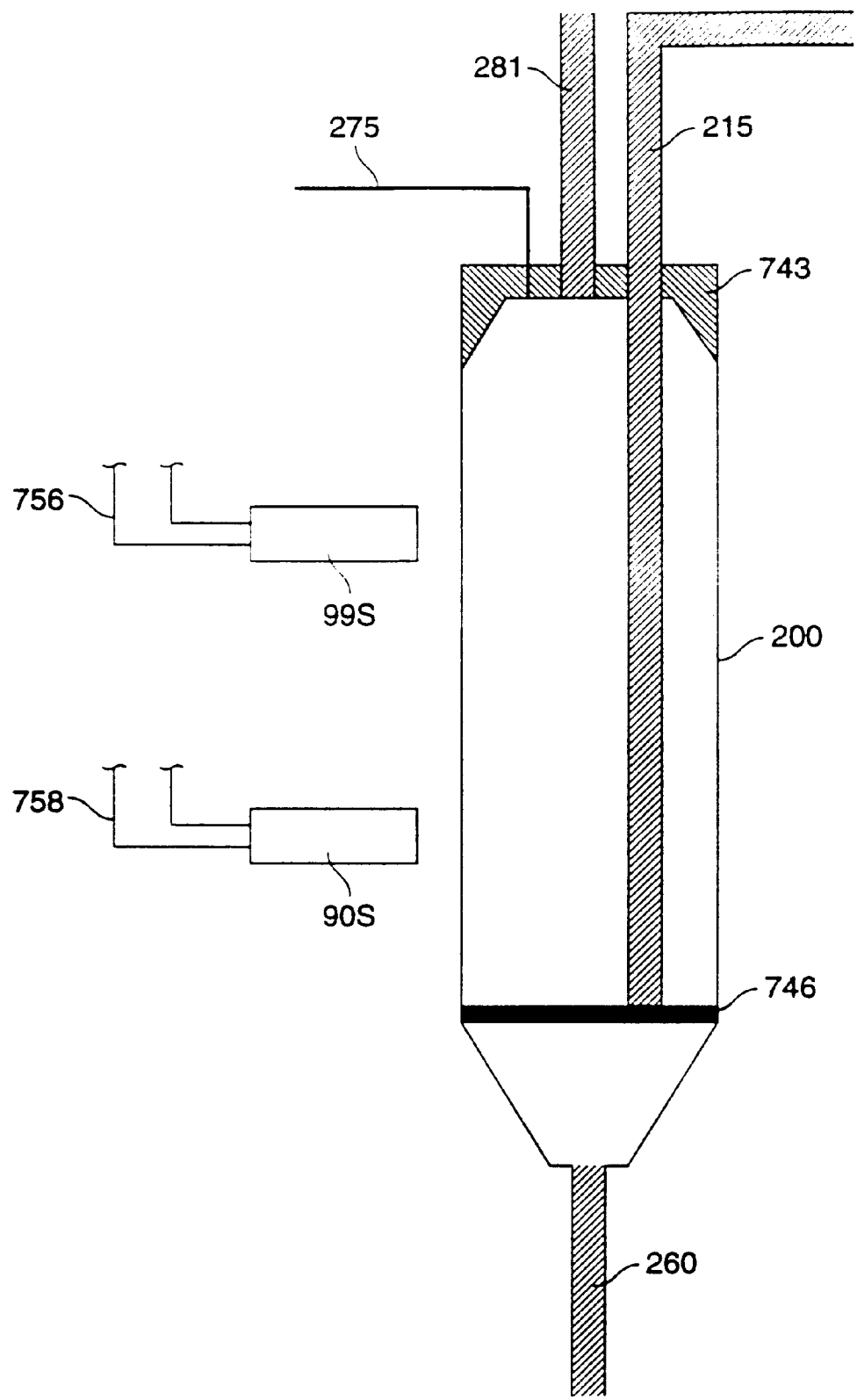
FIG. 13 shows a parent vessel.

FIG. 13 shows in greater detail the parent vessel of the present embodiment. Parent vessel 200 has, for example, a volume of approximately 30 mL. A tube 260 is sealingly connected to the bottom end of parent vessel 200 for transferring a reagent or argon to and from delivery system PDS 265 (not shown in FIG. 13). A frit or filter 746 is fitted near the bottom of parent vessel 200 to prevent substrates from entering tube 260. There is a removable cap 743 fitted on the top end of parent vessel 200 for adding and removing material. Tube 215 fitted through cap 743 transfers material between parent vessel 200 and top common manifold 212 in a reaction vessel bank (not shown in FIG. 13). Tube 215 extends through cap 743. A pressurized argon/vent line 275 also extends through cap 743. An optional rinse line 281 connects to a solvent source for delivering pressurized solvent to the interior walls of parent vessel 5 to rinse the interior walls.

FIG. 13 shows two capacitive sensors 90S and 99S (Model 18-08 by Electromatic Control Corp. of Hoffman Estates, Ill.) mounted near the exterior of parent vessel 200. Each capacitive sensors 90S or 95S detects the presence of a liquid in its vicinity and transmits sensor data to a control computer (not shown) via wires 756 and 758 respectively. Capacitive sensor 99S is used for detecting the level of reagents added to the parent. Capacitive sensor 90S is for detecting the level of bead suspension for redistribution. Both sensor levels can be adjusted according to amount of beads and the number of reaction vessels used. The capacitive sensor data is utilized by the software to control various cycles of the synthesis process.

5. Control System

5.1 Control Computer

The automated synthesizer utilizes a control computer to acquire data from the sensors, and to control the valves and the vortexing motor during the various cycles of the synthesis process. When used in conjunction with the automated synthesizer, any computer including those popularly known as microcomputers, minicomputers, workstations, mainframes, and the like, may be used to process the sensor data and to issue commands to control the valves and the vortexing motor.

Furthermore, sensor data from the sensors in the synthesizer may be acquired by any number of commercially available data acquisition devices using common data acquisition methods. Likewise, the valves and the vortexing motor may be controlled, responsive to an appropriate computer command, by commercially available input/output controllers.

In one embodiment, an IBM-compatible microcomputer (also known as a personal computer or PC) is used as the control computer (Model Gateway 2000 4DX2-50V, by Gateway 2000 Inc. of No. Sioux City, S. Dak.). Within the PC, there are a plurality of expansion slots permitting the addition of various expansion boards. These boards tap into the bus resources of the PC and permit the PC to communicate with the circuitry on the card to perform an electronic function. Certain expansion boards also permit the PC to communicate with external devices and circuitry. For example, a board popularly known as a modem board plugs into an expansion slot on a PC and permits the PC to communicate with another computer having a modem. The use of expansion boards with a personal computer is a matter of common engineering knowledge.

In one embodiment, the automated synthesizer communicates with the PC via a multichannel digital I/O board (Model PCDIO120-P by Industrial Computer Source of San Diego, Calif.). The specification of the PCDIO120-P board is described in detail in Product Manual No. 0043-050-20A which is also available from Industrial Computer Source.

Each PCDIO120-P provides 120 channels of buffered inputs/outputs (I/O) in five 24-channel groups. Each 24-channel group is controlled by a programmable peripheral interface (PPI) 8255A chip. The channels are selectable in set of 8 for either input or output.

Figure 14:
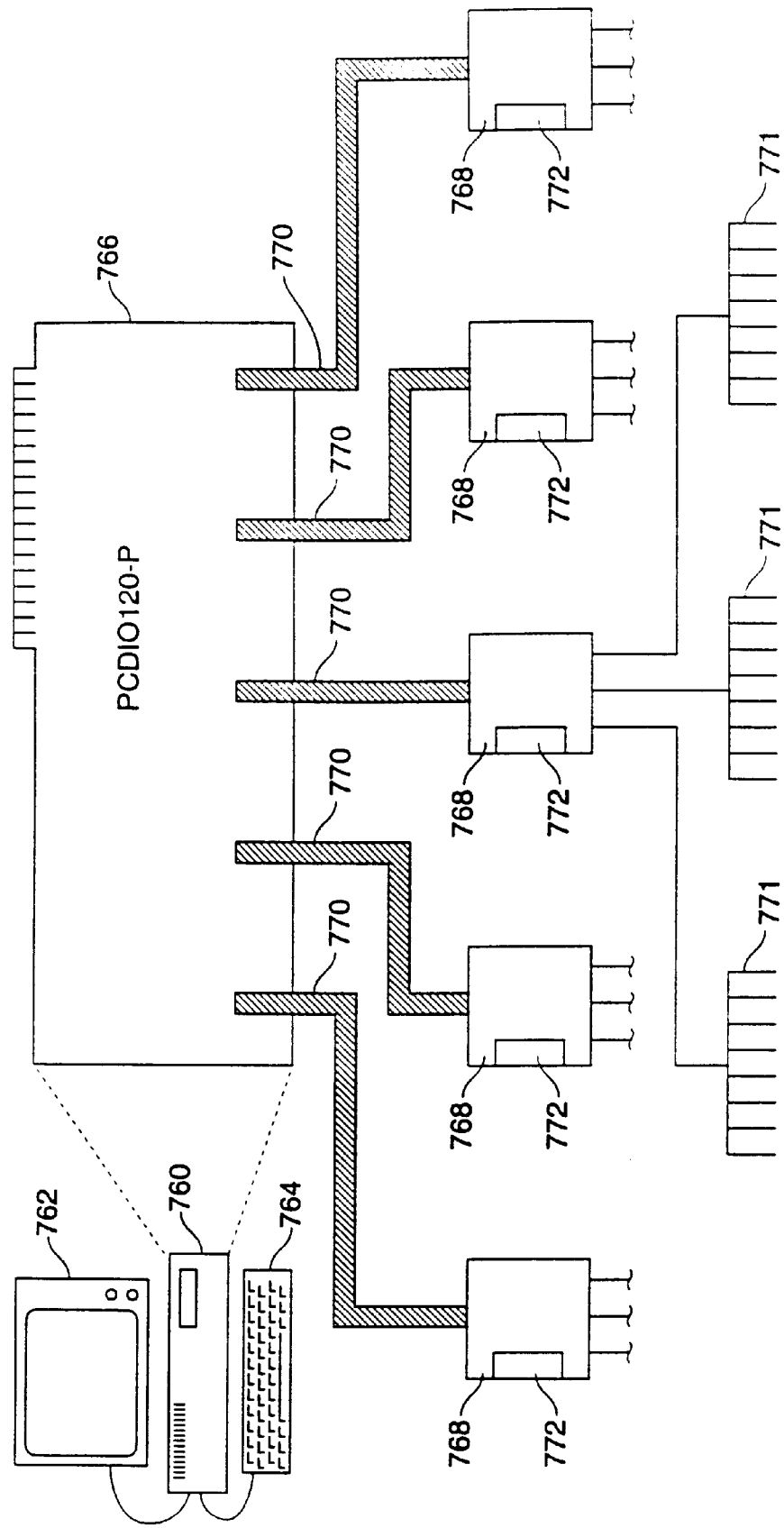
FIG. 14 is a simplified diagram of the electronic hardware for controlling the synthesizer.

FIG. 14 shows a simplified diagram of a portion of the control hardware. A computer 760, such as the PC, having a plurality of expansion slots, connects to a display monitor 762 and a keyboard 764. A PCDP120-P I/O board 766 is inserted into one of the expansion slots to permit the PC to communicate with five controller circuits 768. Each controller circuit 768 communicates with I/O board 766 via a conductor channel 770. In the present embodiment, conductor channel 770 includes a 50-conductor ribbon having the capability to service 24 I/O channels.

5.2 Controller Circuits

The output signals from I/O board 766, typically 15 mA of source current and 24 mA of sink current, are inadequate to operate solenoid valves. Consequently, controller circuits 768 convert the output signals coming from I/O board 766 into power signals having adequate power to actually operate the solenoid valves. Controller circuit 768 has the capability to receive 24 output signals from I/O board 766 and in turn outputs 24 power signals 771 to control various devices of the synthesizer. The 24 power lines 771 of each controller circuit 768 are shown in FIG. 14.

Each controller circuit 768 also provides a central physical location into which sensor data from up to 24 sensor lines, one for each sensor, may be gathered. Data from up to 24 different sensors may be received by a sensor port 772 on each controller circuit 768.

Figure 15:
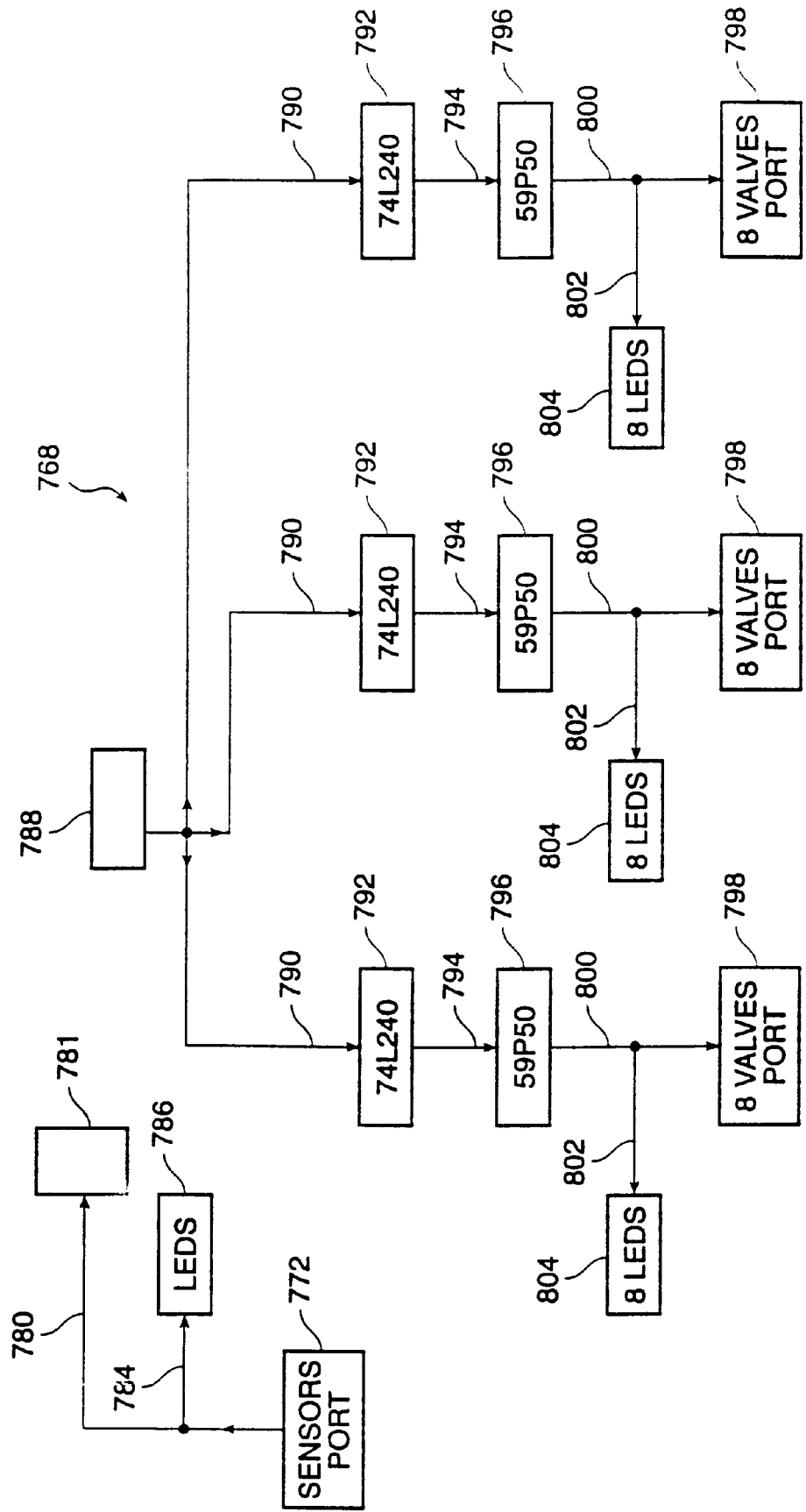
FIG. 15 shows a simplified diagram of the controller circuit.

Thus, each controller circuit 768 can service up to 48 I/O channels, 24 inputs and 24 outputs, of I/O board 766. FIG. 15 shows a representative diagram of a controller circuit 768 according to one aspect of the present invention. A 50-pin header 781 connects the controller circuit 768 to I/O board 766 (not shown in FIG. 15). Header 781 is an input header and is connected via a bus 780 to a sensors port 772. Sensors port 772 comprises headers or connectors for connecting controller circuit 768 with up to 24 input devices such as sensors. Each conductor on bus 780 carries a signal from one sensor to input header 781. FIG. 15 also shows an optional LED bus 784 for carrying LED indicator signals from sensors port 772 to an optional bank of light emitting diodes (LEDs) 786. Each conductor in optional LED bus 784 carries a signal to one LED in bank 786.

FIG. 15 also shows another 50-pin header 788 for connecting controller circuit 768 to I/O board 766 (not shown in FIG. 15). Header 788 is an output header for receiving output signals from I/O board 766. A bus 790 carries up to eight output signals from header 788 to an octal inverter 74LS240 chip 792. Octal inverter 74LS240 chips 792 are manufactured by Texas Instruments, Inc. of Dallas, Tex. A bus 794 carries the inverted buffered output signals from chip 792 to an octal latch driver 796. Latch driver chips 796 are Model MIC59P50, manufactured by Micrel, Inc. of San Jose, Calif. Output signals from each latch driver chip 796 are connected to an output port 798 via a bus 800. An optional LED bus 802 carries LED indicator signals from chip 796 to an optional bank of light emitting diodes (LEDs) 804. Each conductor in optional LED bus 802 carries a signal to one LED in bank 804.

5.3 The Valves

The solenoid valves such as, for example, valves 4–7, 10, 14, 90–91, 100–121, and 129, used in the present embodiment are normally closed unless commanded to open. Consequently, the default state for all valves in the synthesizer is off. Safety is ensured because no material is permitted to flow when the synthesizer is in its default state. When open, valves use power and heat up. Besides the obvious drain on the system power, hot valves may adversely affect the chemicals passing through their ports. Because it normally takes a greater amount of power to open a solenoid valve than to keep an already opened valve open, a strike relay such as, for example, a model D1D20 by Crydom, Inc. of Long Beach, Calif., is used to operate the valves. A strike relay such as the D1D20 supplies +12 volts to a valve for a specified period of time, typically 100 milliseconds, to open the solenoid valve from the off state. The period of time during which the strike relay supplies +12 volts can be specified through software control, and the strike is supplied via an I/O channel. Thereafter, the strike relay supplies a reduced voltage, typically half the rated voltage or approximately 6 volts in the present embodiment, to keep the solenoid valve open. Consequently, less energy is required to operate the valves and less heat is produced.

The present invention provides for four separate power supplies. A first power supply outputs +5 volts to power the TTL chips such as those found on controller circuits 768. A second power supply outputs +32 volts for use by the stepper motor. A third power supply provides +12 volts to activate the solenoid valves. An optional fourth power supply also provides +12 volts for use by the sensors. A separate fourth power supply for the valves ensures that any noise generated by the valves as they open and close does not interfere with sensor operation.

In its default state, all valves are closed. As an additional safety measure, the synthesizer further provides for a solid state watchdog relay to shut off all valves in the event the control computer malfunctions. A solid state watchdog relay such as a Model SM-WDT5 by Brentek International (available from Industrial Computer Source of San Diego, Calif.) is interposed between the control computer and the power supply to the valves. A software-generated pulse is transmitted from the control computer to the watchdog relay on one of the I/O channels. When the pulse is absent, e.g., upon CPU failure, latch-up or power failure, the watchdog relay shuts down the power supply for the valves, thereby closing all valves.

6. Control Software

The control software will now be discussed in detail with reference to the flow charts of FIGS. 16–24. These flow charts illustrate the commands issued by the control computers or completing relevant phases of the synthesis process. To simplify the discussion below, it is assumed that at all relevant times, the valves of the pressurized delivery system receive the appropriate commands from the control computer to deliver the desired reagent to the reaction vessel bank valve.

Figure 16:
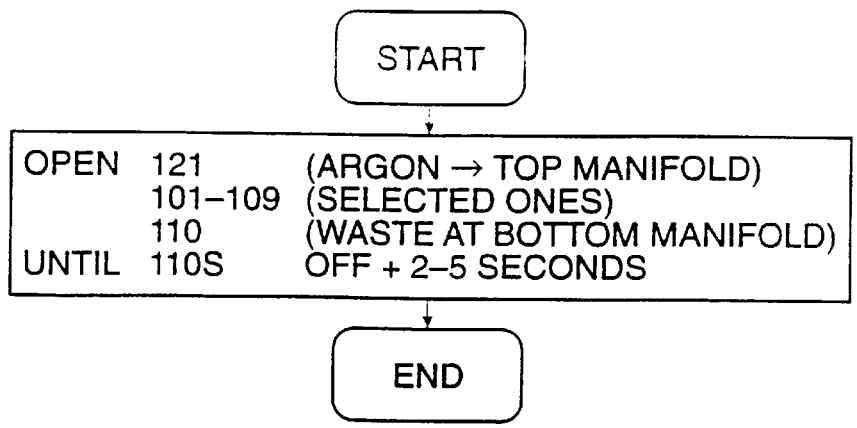
FIG. 16 shows the steps taken by the control computer to drain the reaction vessels of all liquids.

FIG. 16 is a flow chart illustrating the combination of commands issued by the control computer for draining reaction vessels 201–209 of their contents. Before draining, reaction vessels 201–209 contain a liquid or a bead suspension. An argon supply valve 121, connected to top common manifold 212, receives an open command and opens to pressurize top common manifold 212 with argon. At the same time, selected 3-port valves 101–109 open to permit a liquid from reaction vessels 201–209 to enter lower manifold 214. Only selected valves 201–209 open because not all reaction vessels 201–209 are used during some coupling reactions. If a reaction vessel sits empty throughout a synthesis session, there is no need to drain its contents. Waste valve 110 in bottom manifold 214 opens to permit fluid exit. As a consequence of the pressure differential, argon pressure pushes fluid from reaction vessels 201–209, through lower manifold 214, and out waste valve 110. When sensor 110S turns off, signifying that no liquid is left to drain, the valves stay open an additional 2–5 seconds to ensure all liquids are drained from the reaction vessel bank.

Figure 17:
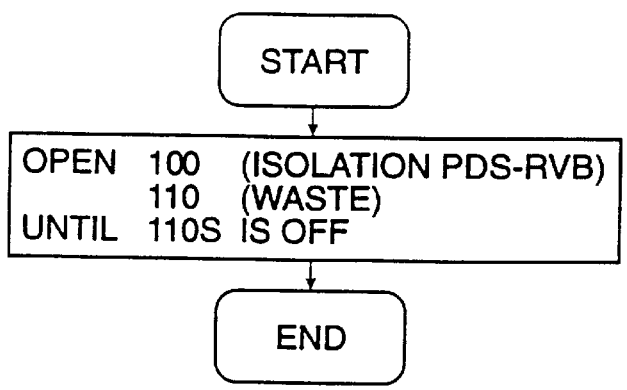
FIG. 17 shows the steps taken by the control computer to clear the bottom manifold of material.

FIG. 17 depicts the combination of commands issued by the control computer to clear lower manifold 214. At the start step, there is material in lower manifold 214. Thereafter, isolation valve 100 opens to permit pressurized argon from PDS 265 to enter lower manifold 214. Simultaneously, waste valve 110 opens to vent material from lower manifold 214. Material exits from lower manifold 214 until no material is left. The valves return to their default state when optical sensor 110S detects no material in the waste tube.

Figure 18:
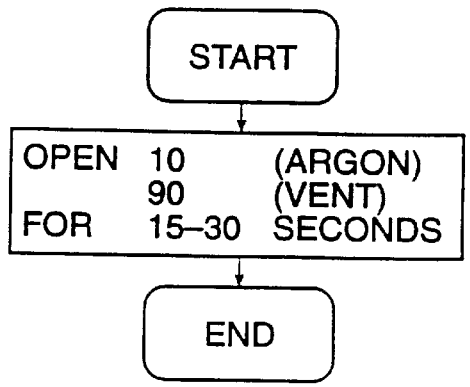
FIG. 18 shows the steps taken by the control computer to agitate the contents of the parent vessels.

FIG. 18 shows the set of commands issued by the control computer to mix the contents of parent vessel 200. The system introduces argon into parent vessel 200 from below to mix the contents. The argon bubbles agitate the contents of parent vessel 200 as they rise from the bottom of the parent vessel to the surface of the contents inside the parent vessel. Again, all valves which have not been expressly commanded to stay open are in their default state. Valve 100 opens to introduce pressurized argon from PDS 265 to the bottom of the parent vessel to agitate the contents within. Valve 90 also opens to vent argon from the parent vessel. Valves 100 and 90 return to their default state after approximately 15 to 30 seconds.

Figure 19A:
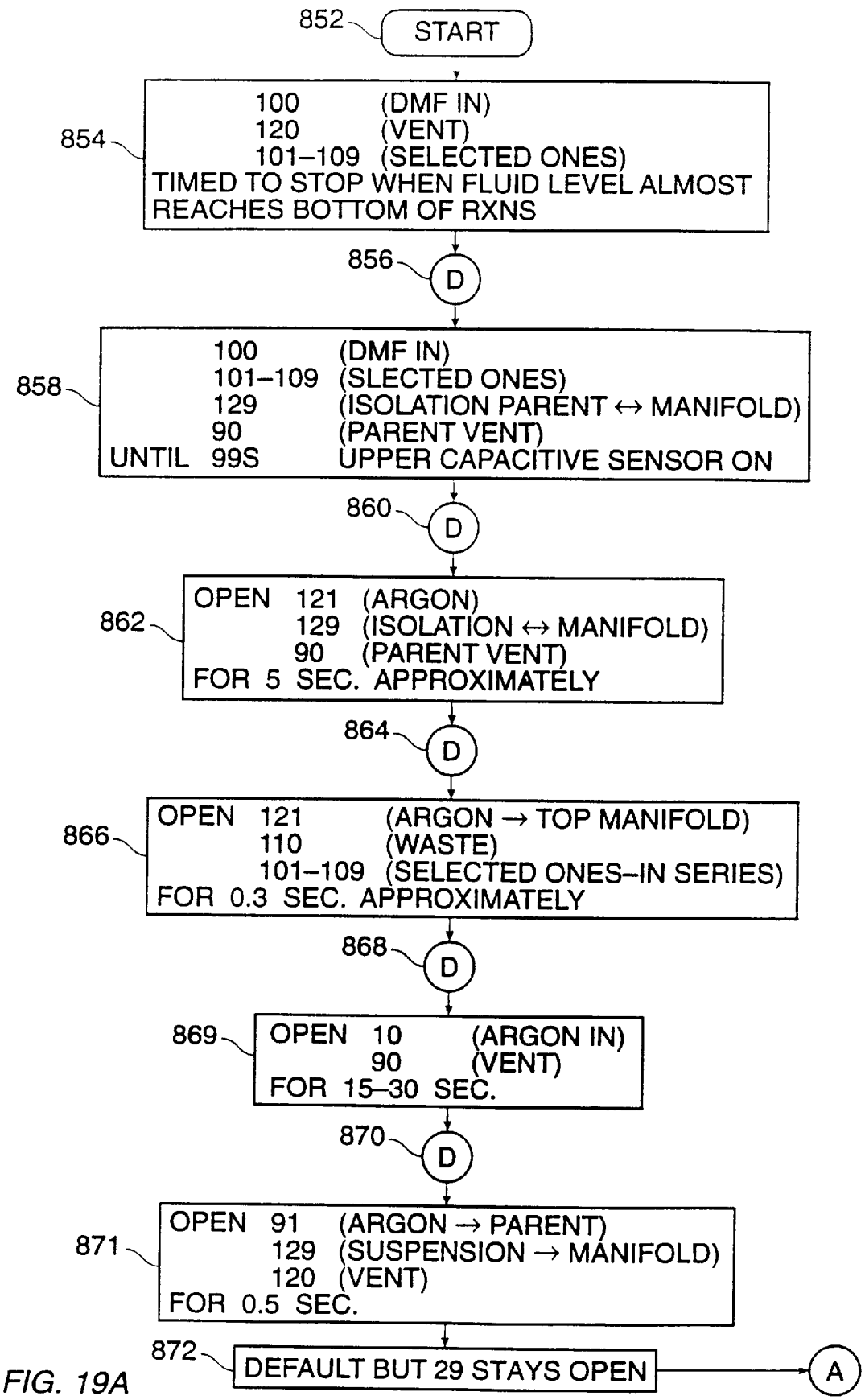
FIGS. 19A and 19B show the steps taken by the control computer to reallocate the bead suspension from the parent vessel to the reaction vessels.
Figure 19B:
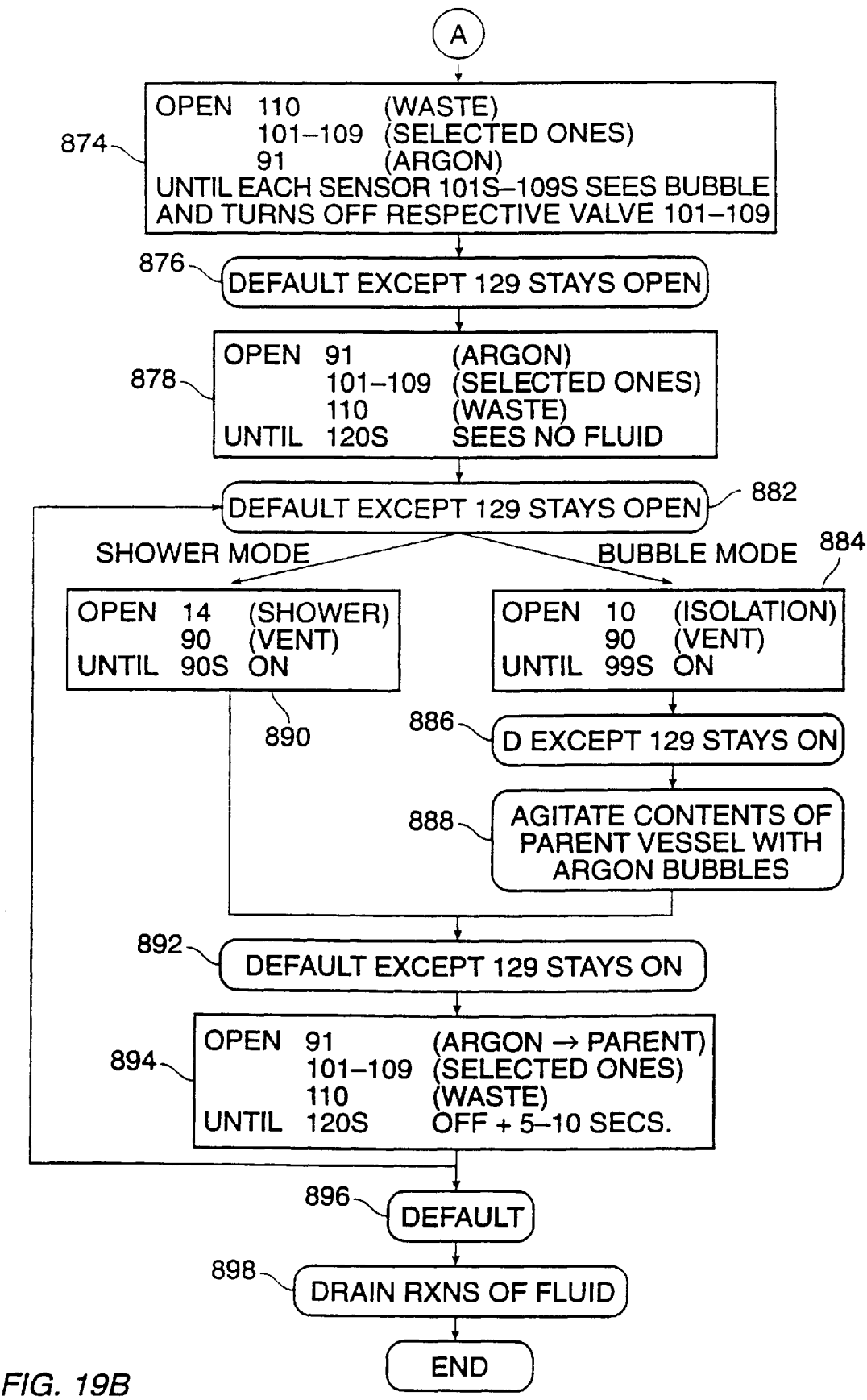

FIGS. 19A and 19B depict the sequence of commands issued by the control computer to allocate bead suspension from the parent vessel to the various reaction vessels. The sequence of commands advantageously permits, as will be seen, the bead suspension to be distributed evenly among the reaction vessels regardless of the distance between that reaction vessel and the manifold port through which the bead suspension enters. At the start of the allocation cycle, the reaction vessel bank contains only argon, and the parent vessel contains a bead suspension at step 852.

First, the reaction vessel bank is partially filled at step 854 with DMF to displace the argon that exists in the reaction vessel bank prior to the reallocation phase. Isolation valve 100 opens to permit pressurized DMF to enter the lower manifold from the pressurized delivery system. Valves 101–109 open to permit DMF to rise toward the reaction vessels. Valve 120 opens to vent argon from the top common manifold. Valves 100, 101–109, and 120 return, preferably in series, to their default state after a preprogrammed time period of 3 seconds each. Reaction vessels 201–209 are then mixed to dislodge bubbles. Valves 100–109 open again for 3 seconds. At the expiration of this preprogrammed time period, the level of DMF in each tube 241–249 leading to the reaction vessels will be near the top common manifold 212.

The reaction vessel bank and parent vessel 200 are then filled with DMF at step 858. Valve 100 opens to permit pressurized DMF to enter the reaction vessel bank from PDS 265. Valves 101–109 open to continue filling the reaction vessel bank with DMF. Valve 129 opens to permit the DMF which overflows the reaction vessel bank to enter parent vessel 200. Valve 90 also opens to vent the displaced argon from parent vessel 200. The filling continues until the level of fluid in parent vessel 200 rises to the level of upper capacitive sensor 99S when sensor 99S detects DMF within its detection envelope. The reaction vessel bank is then completely filled. Parent vessel 200 fills up to approximately the level of second capacitive sensor 99S. Valves 90, 100, 101–109 then return to their closed state at step 860.

Next, the top common manifold is cleared of DMF at step 862. Valve 121 opens to pressurize the top common manifold with pressurized argon. Valve 129 opens to permit DMF to enter the parent vessel from the top common manifold. Valve 90 opens to vent the displaced argon from the parent vessel. DMF from the top common manifold is thereby transferred to the parent vessel. The parent vessel is designed to have a sufficient volume to accept the additional DMF without overflowing. After a preprogrammed time period of five seconds, valves 90, 121, and 129 return to their default state at step 864. The preprogrammed time period is variable but must equal or exceed the time it takes to clear the top common manifold of DMF.

Had the reaction vessels not been prefilled with DMF prior to the introduction of the bead suspension, i.e., had the reaction vessels been empty, an uneven distribution of bead suspension would occur. If the reaction vessels were empty, the reaction vessel which is the closest to the manifold port through which the bead suspension enters from the parent vessel would fill up first. There may be no bead suspension left for some reaction vessels if a few were allowed to fill up excessively.

The present invention employs a novel method for controlling the volume at which a reaction vessel accepts the bead suspension. First, at step 866, a small column of argon is introduced to the top of each tube which connects the reaction vessels to the top common manifold. To create this argon bubble, valve 121 opens to permit pressurized argon to enter the top common manifold. Selected valves 101–109 open to permit some DMF to drain from the reaction vessels to the lower manifold. Valve 110 opens to vent the displaced DMF from the bottom manifold. After 0.3 seconds, a small column of argon appears at the top of the tube which connects the reaction vessel to the top common manifold. Valves 101–110, and 121 then return to their default state at step 868.

A portion of the bead suspension is then introduced to the top common manifold at step 870. This step is timed according to a preprogrammed time period so that the bead suspension that enters the top common manifold displaces most of the argon existing within the top common manifold without flowing past the manifold port into which the last reaction vessel tube, e.g., the reaction tube associated with sensor 109S, connects. A preprogrammed period of 0.5 seconds has been found to be satisfactory. To introduce this portion of the bead suspension to the top common manifold, valve 91 opens to pressurize the parent vessel with argon.

Valve 129 opens to permit the bead suspension to flow into the top common manifold. Valve 120 opens to vent the argon existing in the top common manifold. After the expiration of the previously discussed preprogrammed time period, valves 91 and 120 return to their default state at step 872. Most importantly, valve 129 continues to stay open to prevent beads and polymers from being damaged due to the closing action of the valve. In the present embodiment, 2-port valve 129 continues to receive the command signal from the control computer to stay open in the manner discussed earlier. However, valve 129 may be a latch valve which toggles between the open and shut states upon receipt of a command pulse from the control computer. If valve 129 is a latch valve and is already open, no action needs to be taken by the control computer to keep latch valve 129 open.

FIG. 19B is a continuation of FIG. 19A. After some argon which existed in top common manifold 212 has been displaced, the rest of the bead suspension is transferred to top common manifold 212 at step 874. Valve 91 opens to pressurize parent vessel 200 with argon. Valve 129 which has been kept open permits the pressurized bead suspension to enter top common manifold 212. Selected valves 101–109 open to permit the DMF within reaction vessels 200 to exit into lower manifold 214. Valve 110 opens to drain DMF from lower manifold 214. Partly due to the resistance of the bead suspension, DMF recedes down selected reaction tubes 201–209 relatively slowly. The DMF displaced from selected tubes 221–229 connecting selected reaction vessels 201–209 with top common manifold 212 is replaced with the bead suspension. The column of suspension-bubble-DMF advances slowly downward towards lower manifold 214.

The column of bubble introduced earlier also advantageously serves as a volume marker, i.e., provides a way for the control computer to determine when each reaction vessel has received a sufficient amount of bead suspension. The column of bubble stays trapped between the column of DMF and the column of suspension because of the surface properties of the teflon and the high contact angle between the bead suspension and teflon. As discussed earlier, the optical sensors used in the present embodiment can detect the presence or absence of a liquid column inside a substantially translucent teflon tube. As DMF is replaced by the downwardly advancing mass of bead suspension, the bubbles move down into the reaction tubes and into the tubes which connect the reaction vessels to the lower manifold. At the moment the argon bubble is detected by an optical detector 101S–109S on its downward movement, that detector is momentarily turned off. The sensor data, as discussed earlier, is communicated to the control computer which promptly issues a command signal to shut off a respective valve 101–109. After all valves 101–109 have been turned off, the bead suspension transfer is restarted and continues at step 878 until acoustic sensor 120S detects no fluid in the tube connecting the parent vessel with the top common manifold. At step 882, all valves except valve 129 return to their default state. As discussed, valve 129 stays open to avoid damage to the beads and valve 129.

The synthesizer at this point has strained suspension in its reaction vessels, and possibly some bead suspension residue in the parent vessel. To make sure all the beads are transferred to the reaction vessels, a rinsing process comprising at least one rinse cycle is employed.

In one embodiment, the parent vessel is refilled with DMF and mixed to loosen any bead suspension residue which may have clung to the interior walls or frit of the parent vessel. First, at step 884 the parent vessel is refilled with fresh DMF. The refilling is accomplished by opening valve 10 to permit DMF to enter the parent vessel from the pressurized delivery system. Valve 90 also opens to permit displaced argon to exit the parent vessel. When the level of DMF in the parent vessel rises to the level of the top capacitive sensor 99S, top capacitive sensor 99S is turned on. This sensor data is received by the control computer which promptly issues a command at step 886 to return all valves except valve 129 to their default state. The parent vessel is then mixed at step 888 by introducing argon bubbles to the parent vessel in the manner previously discussed.

Alternatively, the interior walls of the parent vessel are "showered" at step 890 with DMF sprays to rinse down any bead suspension residue which may have cling to the wall. Valve 14 opens to permit sprays of DMF to wash down the walls. Valve 90 opens to vent the replaced argon from the parent vessel. The interior wall continues to receive sprays of DMF until the level of DMF in the parent vessel rises to the level of lower capacitive sensor 90S and turns it on. The contents of the parents are then stirred by argon bubbles in the manner previously discussed. This sensor data is received by the control computer which promptly issues a command at step 892 to return all valves except valve 129 to their default state.

The mixture of DMF and bead suspension is then transferred to the reaction vessels at step 894 by opening valve 91 to pressurize the parent vessel with argon and to transfer the mixture to the top common manifold through valve 129 which has remained opened through out the rinsing process. Selected valves 101–109 open to permit fluid to flow from the reaction vessels to the lower manifold. Valve 110 opens to drain DMF from the bottom manifold. The frits at the bottom of the reaction vessels strain all beads inside the reaction vessels. Eventually, the parent vessel is drained. Sensor 120 turns off when no fluid is present in the tube connecting the parent vessel with the top common manifold. This sensor data is communicated to the control computer to signify that no fluid is left in the parent vessel to transfer. The control computer continues to open valve 91 for another 5–10 seconds to pressurize the top common manifold and to move any remaining mixture into the reaction vessels. After 5–10 seconds, all valves except valve 129 are returned to the default state. One rinse cycle is completed.

As discussed earlier, a plurality of rinse cycles may be employed to ensure that substantially all bead suspension from the parent vessel is transferred to the reaction vessels. Three rinse cycles have been found to be satisfactory.

When all rinse cycles are completed, all valves including valve 129 are returned to the default state at step 896. Note that valve 129 remains open throughout the bead suspension reallocation process, including the rinsing process, to minimize any damage to beads and polymers. The reaction vessel bank is then drained of all fluids in the manner earlier discussed at step 898.

Figure 20:
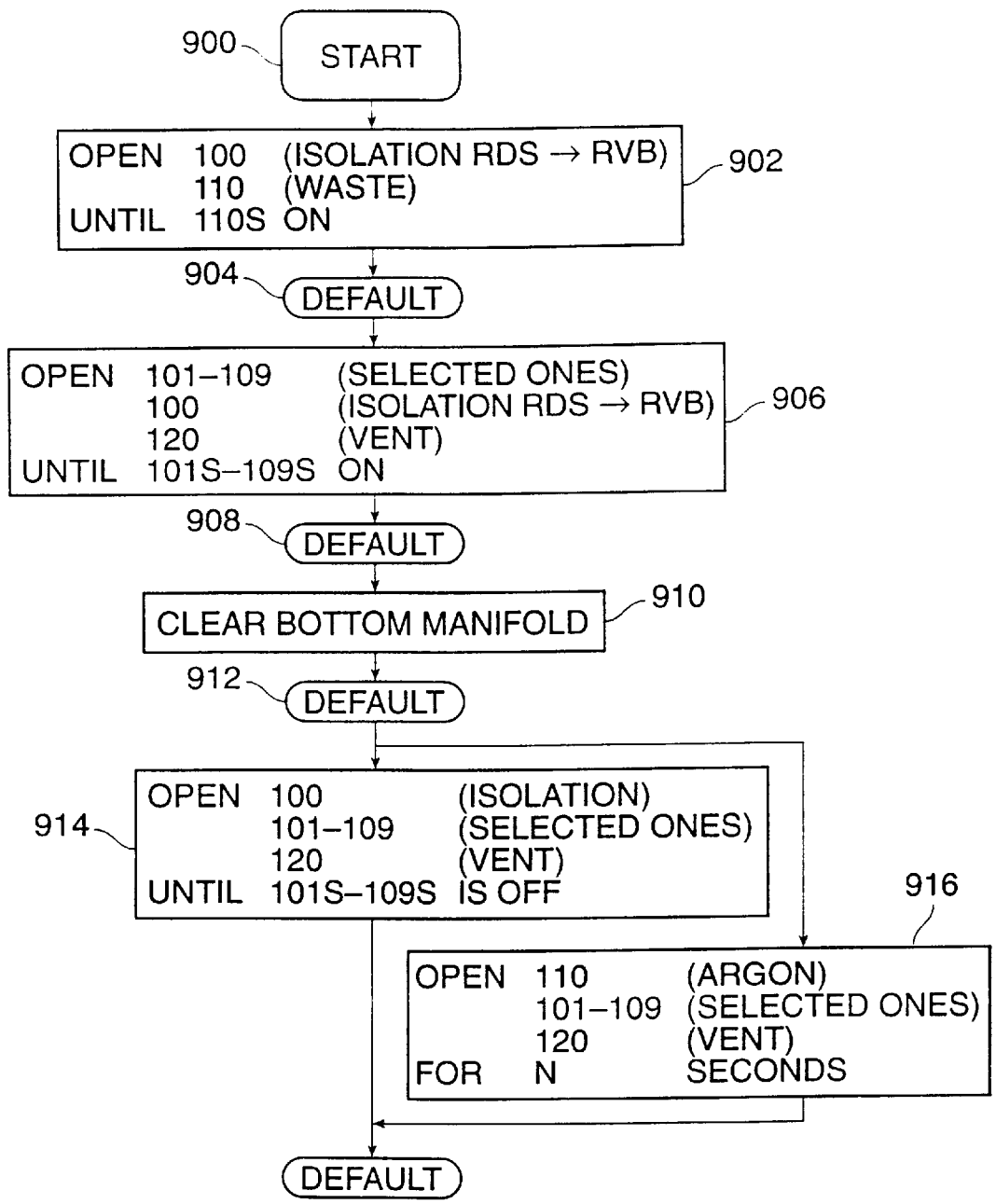
FIG. 20 shows the steps taken by the control computer to fill the reaction vessels with reagents from the pressurized delivery system.
Figure 21A:
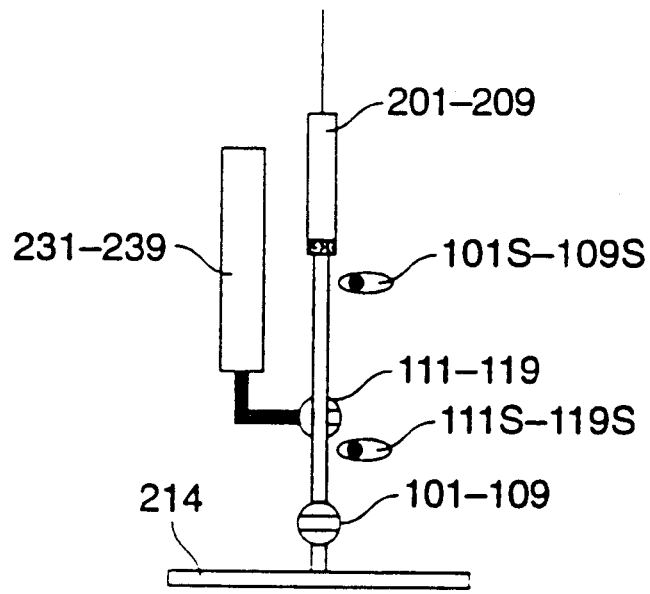
FIGS. 21A–21D schematically illustrate the steps taken by the control computer to fill the reaction vessels with reagents from the pressurized delivery system.

FIG. 20 is a flow chart showing the sequence of commands issued by the control computer to fill the reaction vessel with a reagent from the delivery system. The steps discussed in connection with FIG. 20 are also schematically illustrated in FIGS. 21A–21D. This process assumes that the lower manifold is filled only with inert argon at step 900. FIG. 21A graphically shows a relevant portion of the reaction vessel bank having an empty manifold. The lower manifold is first filled with a reagent at step 902. Valve 100 opens to permit the reagent to enter the lower manifold, and valve 110 opens to vent the argon displaced from the lower manifold. When the reagent is detected by sensor 110S, all valves return to default at step 904.

Figure 21B:
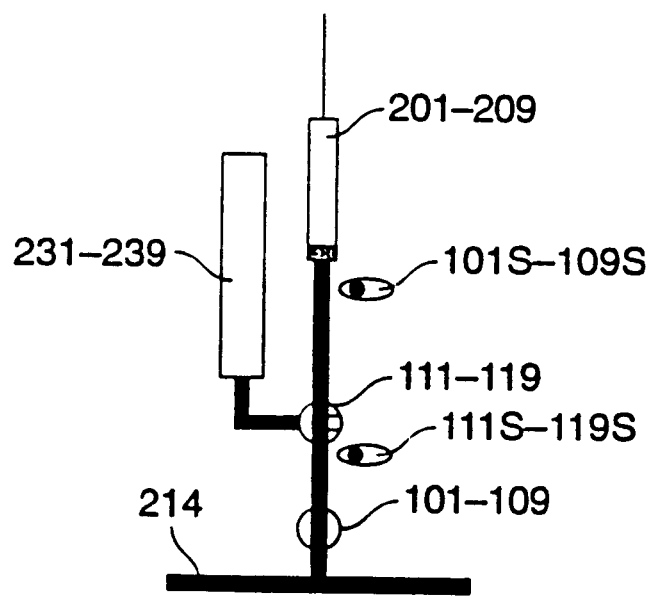

Next, the reagent is pushed up the tubes connecting the reaction vessel with the lower manifold at step 906. The pushing process may be carried in parallel to save time or in series. Valve 100 opens to permit pressurized argon from the pressurized delivery system to enter the lower manifold. Selected valves 101–109 open, serially or in parallel, to permit the reagent to enter the tube connecting the reaction vessel with lower manifold. When the reagent level in a tube reaches the level of the upper light sensor 101S–109S, the light sensor turns on, and the control computer promptly turns off an associated valve 101–109. When all sensors 101S–109S are on, all valves are returned to the closed state at step 908. FIG. 21B schematically illustrates the result after the this flushing step is completed.

Figure 21C:
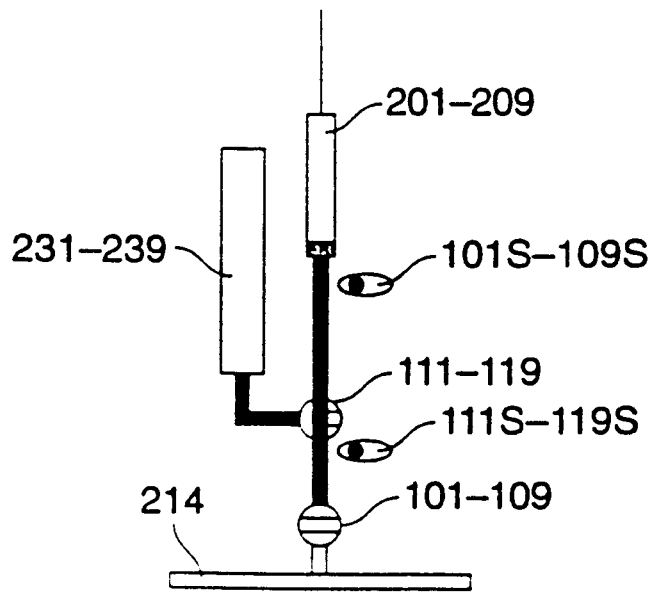

The bottom manifold is then cleared in the manner earlier discussed at step 910. FIG. 21C shows a relevant portion of the reaction vessel bank having a cleared manifold and a column of reagent inside the portion of the tube between a top optical sensor, e.g., 101S, and a valve, e.g., 101. After the bottom manifold is cleared, all valves are again returned to default at step 912. The reagent in the tubes are then pushed up into the reaction vessels through the frits. To push the reagent into the reaction vessels, vent valve 110 opens to permit argon from the pressurized delivery system to pressurize the lower manifold. Vent valve 120 also opens.

Figure 21D:
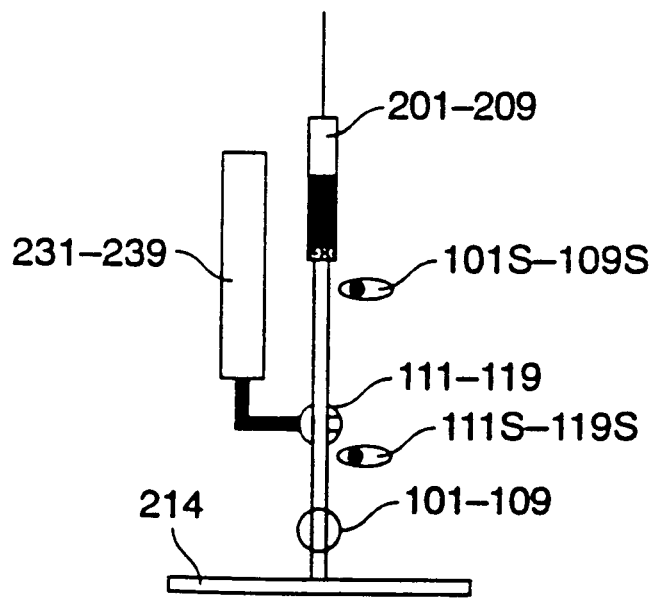

Again, the reagent may be pushed into the reaction tubes serially or in parallel. To push the reagent up into the reaction tubes serially, each valve 101–109 turns on successively at step 914 until its associated sensor 101S–109S detects the absence of a fluid and the control computer turns off that valve. When all sensors 101S–109S are off, all reaction tubes are filled. To push the reagent up into the reaction tubes in parallel, selected ones of valves 101–109 open in parallel at step 916. After a preprogrammed period of time, all valves close in parallel. A preprogrammed time period of 0.5 seconds to 1 second has been found to be satisfactory. The longer the time period, the more volume is pushed into the reaction vessels. FIG. 21D shows a diagram of the reaction vessel after being filled.

Note that the volume of reagent to be pushed up into the reaction tubes also can be easily changed by varying the length or diameter of tubings between valves 101–109 and sensors 101S–109S. This change can be easily accomplished by substituting the tube which connect a reaction vessel to an injection valve, e.g., valve 111, with a tube having a different length or cross-sectional dimension.

Figure 22:
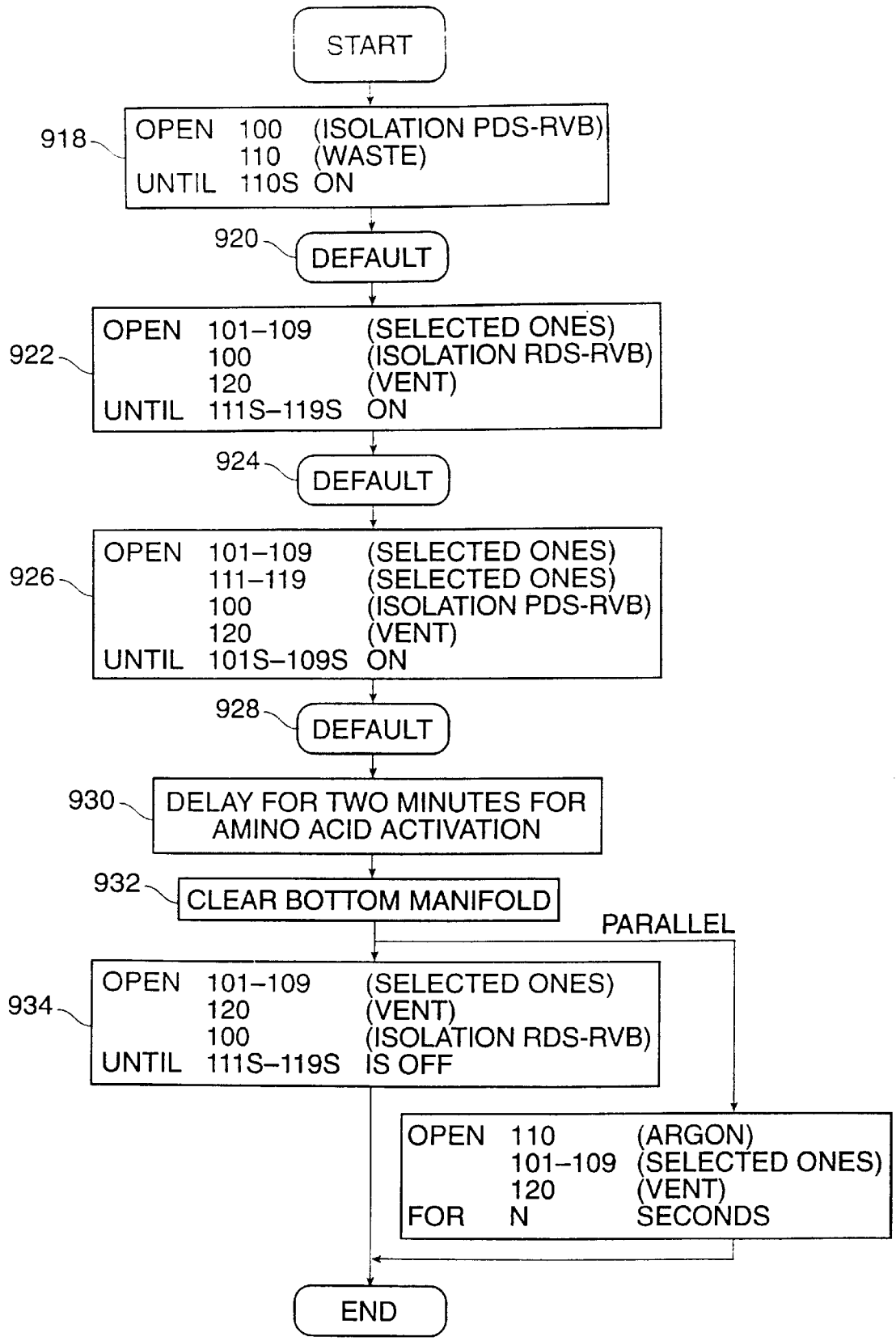
FIG. 22 shows the steps taken by the control computer to introduce amino acid monomers into the reaction vessels.
Figure 23A:
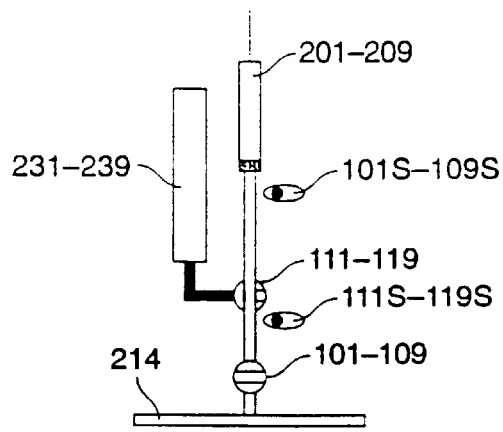
FIGS. 23A–23C schematically illustrate the steps taken by the control computer to introduce amino acid monomers into the reaction vessels.
Figure 23B:
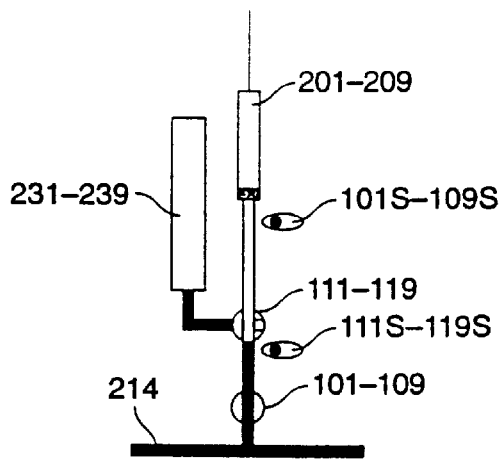
Figure 23C:
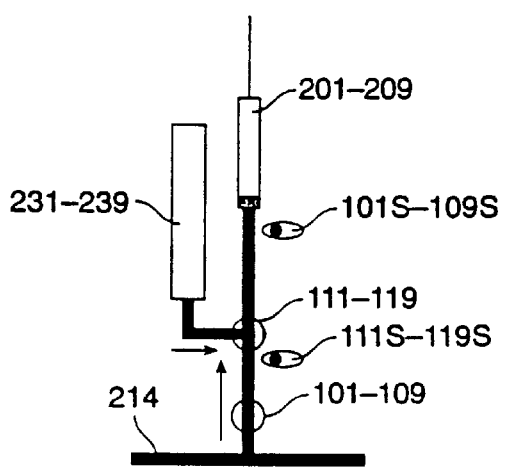

FIG. 22 is a flow chart showing the sequence of commands issued by the control computer to inject activated amino acid reagents into the reaction vessels. FIGS. 23A–23C schematically illustrate the relevant steps of the amino acid injection process. Again, it is assumed that the lower manifold is cleared, i.e., contains only argon, at the start. FIG. 23A shows a diagram of the reaction vessel, the lower manifold, the valves, the sensors, and associated tubes at the start. The manifold is first filled at step 918 with amino acid activating reagents such as 0.2M HBTU and 0.6M DIEA in a solution of 3:1 DMF to DCM. The manifold is filled in the manner discussed in connection with FIG. 20, i.e., open valves 100 and 110 until sensor 110S is turned on. Thereafter, all valves close at step 920.

The activating reagents then enter the tubes connecting the reaction vessels with the lower manifold. Valves 100 and 120 open to let pressurized activating reagent enter the lower manifold at step 922. Selected ones of valves 101–109 open until the lower optical sensors 111S–119S senses fluid presence. All valves again close at step 924. FIG. 23B graphically shows the presence of fluid in relevant portions of the reaction vessel bank after this initial filling step.

To accomplish the injection, valves 100 and 120 again open to let pressurized activating reagents enter the lower manifold at step 926. Selected ones of valves 101–109 open in parallel to permit a column of pressurized activating reagent to advance up the aforementioned tube. Simultaneously, associated ones of valves 111–119 open to inject amino acid into the upwardly advancing column of pressurized activating reagent and to mix with the activating reagent. FIG. 23C graphically shows this injection step.

When each sensor 101S–109S detects a fluid presence, the control computer turns off a valve 101–109 which is associated with that sensor. When all valves 101–109 close at step 928, all valves of the reaction vessel bank return to the default mode. The mixture of amino acid and activating reagent is preferably permitted to stay in the aforementioned tube for about two minutes to ensure proper activation at step 930.

Thereafter, the bottom manifold is cleared at step 932 in the manner discussed earlier in connection with FIG. 17. The column of mixture between valves 101–109 and upper sensors 101S–109S are then pushed up into the reaction tubes in the manner discussed in connection with FIG. 22 at step 934.

Figure 24:
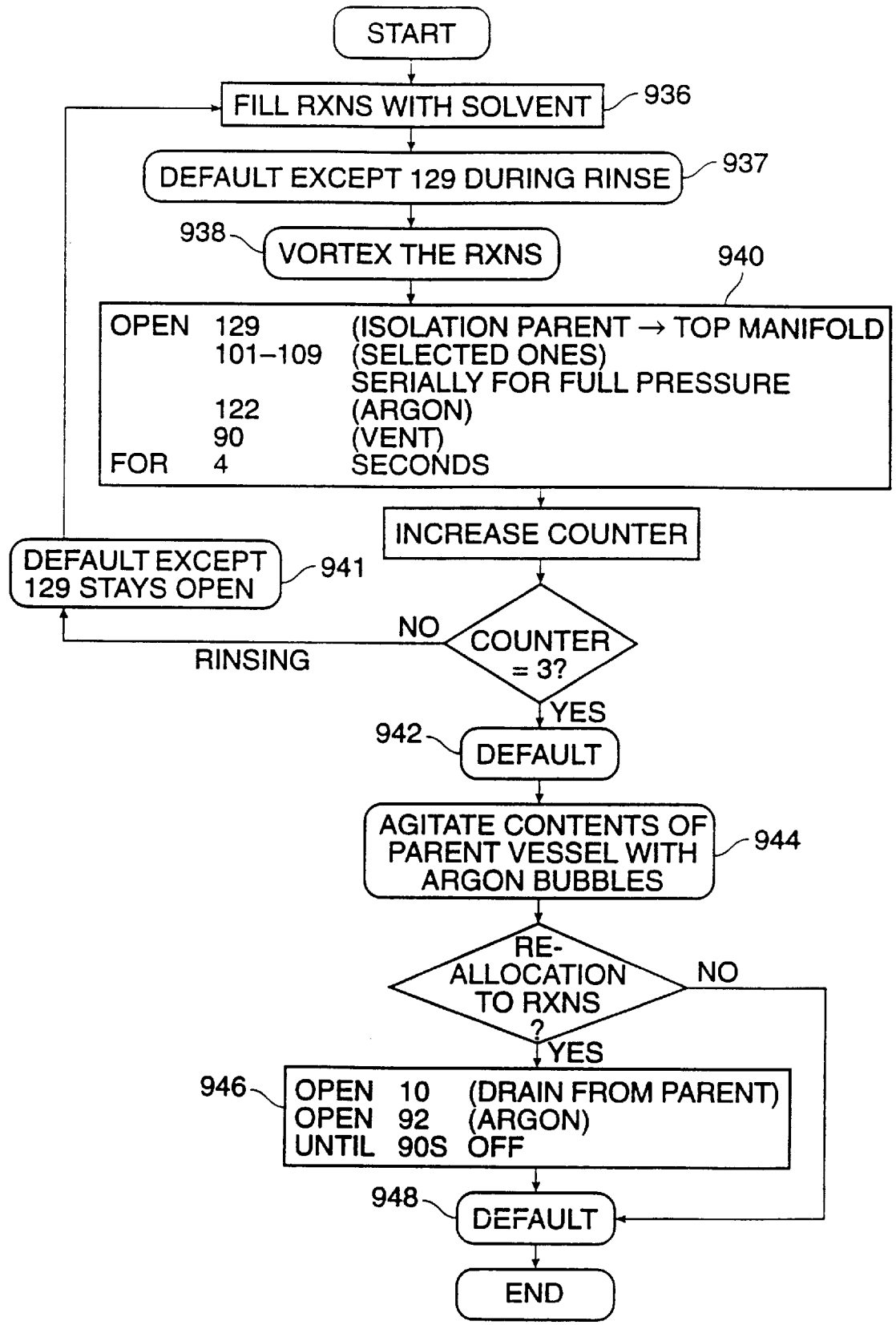
FIG. 24 shows the steps taken by the control computer to transfer the bead suspension from the reaction vessels to the parent vessel for mixing.

FIG. 24 shows the sequence of commands issued by the control computer for transferring the bead suspension within the reaction vessels back to the parent vessel. At the start, it is assumed that the reaction vessels have been drained, and the lower manifold is filled with argon. The reaction vessels are first filled with DMF at step 936 in the manner discussed in connection with FIG. 20. Thereafter, all valves return to default.

Next, the mixture of beads and DMF is vortexed to create a suspension at step 938. The contents of the reaction tubes are transferred to the parent vessel at step 940. Valve 122 opens to pressurize the lower manifold with argon. Valve 129 opens to permit the bead suspension to move from the reaction vessel bank to the parent vessel. Selected ones of valves 101–109 open, preferably in series, to permit argon to blow the contents of each reaction vessel up toward the top common manifold and into the parent vessel. The contents of the reaction vessels are thus transferred to the parent vessel serially. Although the above transfer may also be performed in parallel by opening valves 101–109 simultaneously, serial transfer permits argon pressure within the reaction vessel bank to remain high and is therefore preferable. Furthermore, each of valves 101–109 preferably remains open for about four seconds to ensure that substantially all of the contents of a given reaction vessel are transferred to the parent vessel. During this process, valves 90, 122, and 129 remain open.

After the contents of all reaction vessels are transferred to the parent vessel, the reaction vessels may be rinsed and another transfer process may occur. To rinse the reaction vessels, the above steps are repeated, starting with the refilling of the reaction vessels with DMF at step 936. As shown in steps 937 and 941, valve 129 is kept open during the line cycles to prevent damage to the beads and valve 129. The parent vessel preferably has volume for at least three transfers. At the end of the recombination, the parent vessel is preferably drained by opening valves 110 and 91 until the level of fluid in the parent vessel reaches below lower capacitive sensor 90S and turns that sensor off. Three cycles of rinse have been found to be satisfactory.

Thereafter, all valves including valve 129 return at step 942 to the default state. The contents of the parent vessel are agitated at step 944 to mix the beads from the various vessels in the manner discussed in connection with FIG. 20. If the beads are to be removed from the parent vessel, the parent vessel is preferably drained at step 946 by opening valves 10 and 91 until the level of fluid in the parent vessel reaches below lower capacitive sensor 90S and turns that sensor off. All valves are subsequently returned at step 948 to their default state. The mixture containing beads may then be removed from the parent vessel for use.

Alternatively, the beads may be reallocated to the reaction vessels in the manner discussed in connection with FIGS. 21A–21B. Following the reallocation, all valves return to the default off state.

7. Overall Diagram of Software

Figure 25:
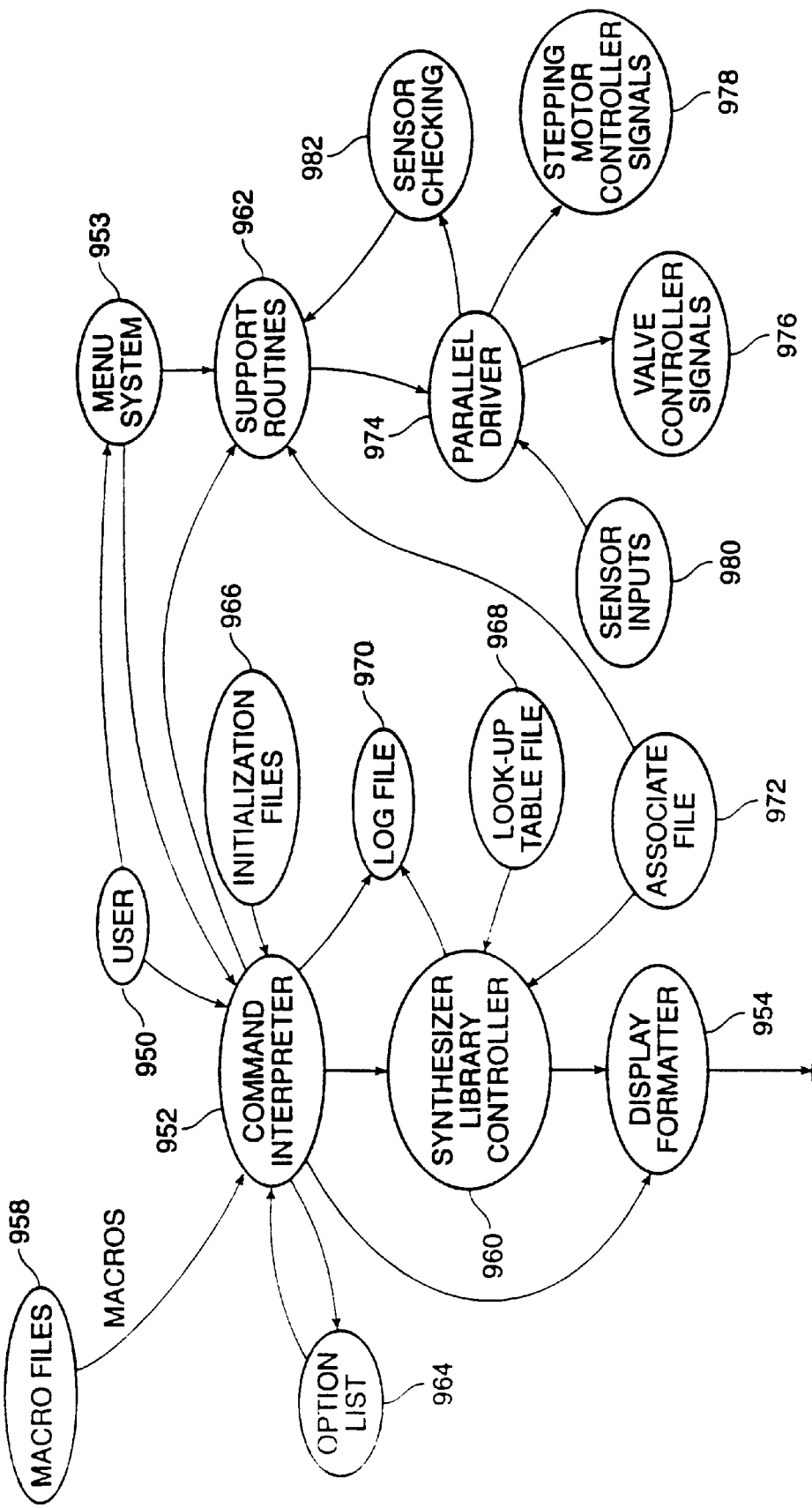
FIG. 25 schematically illustrates the data flow among the major modules of the control software.

FIG. 25 is a flow chart of the source code which is included herein as Appendix I. Module 950 represents the user. A command interpreter 952 accepts the textual commands from the user. Alternatively, the user may enter commands to run the synthesizer using a menu system 953. The commands received by menu system 953 are either converted to a format usable by command interpreter 952, or call a support routine in support routines module 962 directly. Command interpreter 952 also parses the commands entered, textually or otherwise, by the user. Thereafter, the parsed commands call and execute support routines in support routines module 962. Furthermore, the parsed commands are formatted by a display formatter 954 and displayed on a display 762.

Module 958 contains a plurality of macro files. A macro file defines, for example, the sequence of steps that must actually take place to run a synthesis or build a library. At its most basic level, a macro file contains, for example, macros which in turn contains sets of discrete commands for controlling valves and reading sensor information. Macros may utilize other basic macros to perform higher level functions such as draining reaction vessels 201–209.

The macros received by command interpreter 952 from macro files 958 are passed into a synthesizer library controller 960. Synthesizer library controller 960 calls the macros for actual synthesis. For example, one macro may specify the initial global variables that must be set before synthesis begins.

Figure 26:
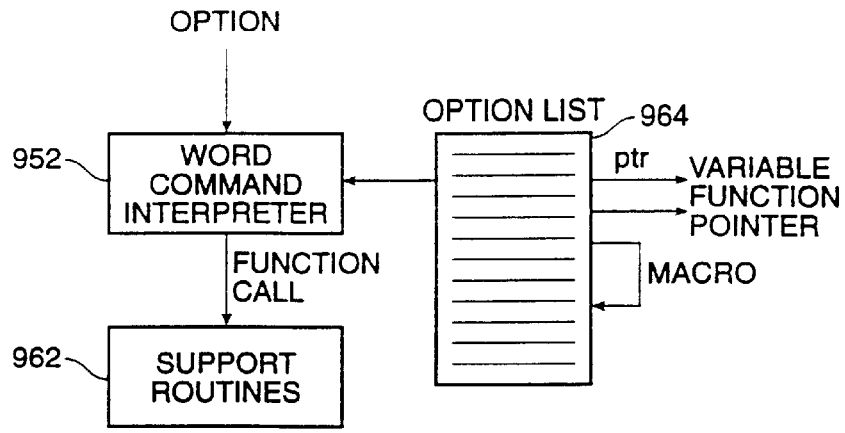
FIG. 26 schematically illustrates the command interpreter structure.

FIG. 25 shows a support routines module 962 for running a variety of support subroutines. One such subroutine is autofill, which is a subroutine for automatically filling the reaction vessels until all sensors are on. Support routines 962 accept inputs from either command interpreter 952 or menu system 953. Option list 964 contains pointers to functions, etc. FIG. 26 shows the inputs and outputs of option list 964 and its relationship with command interpreter 952 and support routines module 962.

There are also initialization files 966 for holding global variables and global settings. Initialization files 966 hold, for example, a value representing the amount of time during which a strike voltage is supplied to a valve to open a closed valve, etc. A lookup table file 968 cooperates with synthesizer command library controller 960 to, for example, permit a monomer to enter appropriate selected reaction vessels. Lookup table file 968 may contain, for example, a listing of each reaction vessel, its corresponding tag monomer, and the list of monomers necessary for synthesizing the desired polymer.

FIG. 25 also shows a log file 970. Log file 970 accepts inputs from command interpreter 952 and synthesizer library controller 960. Log file 970 contains operational data for diagnostic purposes. An entry in log file 970 contains, for example, information relating to the macros called.

An associate file 972 contains a listing of each reaction vessel and its associated valves and sensors. Associate file 972 cooperates with both synthesizer library controller 960 and support routines 962 to simplify the task of addressing each reaction vessel and its associated valves and sensors.

The digital commands outputted by support routines 962 enter a parallel driver 974. Parallel driver 974 may be, for example, PCDIO120-P I/O board 766. Parallel driver 974 outputs valve control signals 976 via its I/O channels to drive the solenoid valves. The valve control signals, as discussed, are further processed by controller circuit 768. Furthermore, parallel driver 974 outputs stepping motor controller signals 978 to control the vortexing stepper motor. Sensor inputs 980 from the optical sensors, the ultrasonic sensor, and ace capacitive sensors of the synthesizer are also received by parallel driver 974 for processing by support routines 962 via sensor checking subroutines 982.

Figure 27:
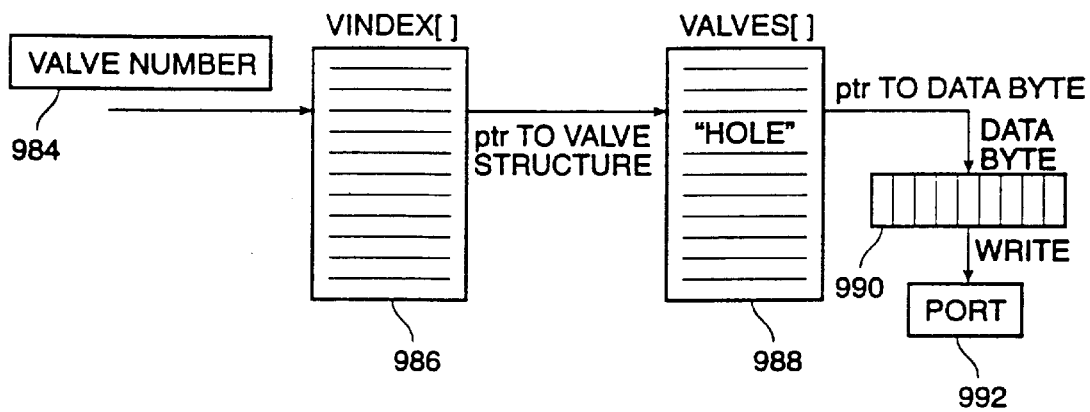
FIG. 27 schematically illustrates the scheme used to access valve data.

FIG. 27 illustrates the data structures necessary to control valves. A valve index VINDEX array 986 accepts a valve number 984 as input and provides a pointer to a VALVES array 988. Each element of VALVES array 988 contains a pointer to a data byte 990. Each data byte 990 contains 8 bits of valve data information. The bit containing valve data information for a given valve is accessible by the address of its data byte 990 and a shift value representing the relative location of that bit within data byte 990. Each bit of data byte 990 may be manipulated to appropriately turn on or off a valve. The valve data information in each bit controls a corresponding valve via output port 992.

Figure 28:
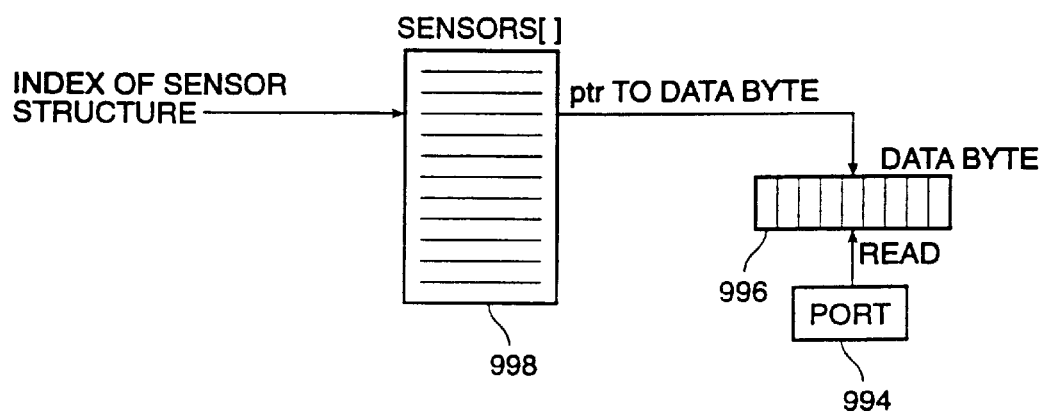
FIG. 28 schematically illustrates the scheme used to access sensor data.

FIG. 28 illustrates the data structures necessary for receiving sensor information from input port 994. The information representing the binary state of each sensor is stored in one bit in a data byte 996. To access the information in data byte 996, a sensor number is used to access SENSOR array 998. Each element of SENSOR array 998 contains a pointer to an appropriate data byte. Each data byte 996 contains 8 bits of sensor data information. The bit containing valve data information for a given valve is accessible by the address of its data byte 996 and a shift value representing the relative location of that bit within data byte 996.

8. EXAMPLES

The following examples are provided to illustrate operation of the invention.

8.1. Example 1

To determine if mixed beads from the parent vessel were being evenly distributed to the reaction vessels, some beads were biotinylated. The biotinylated beads were manually deposited in one reaction vessel. Non-biotinylated beads were manually deposited in the other 8 reaction vessels. The synthesizer transfers all beads from 9 reaction vessels to the parent vessel. A sample was taken from the parent vessel, and fluoresced streptavidin was allowed to bind with biotin on the biotinylated beads. Florescence Activated Cell Sorter (FACS) analysis shows that approximately 9.1% of the beads in the parent vessel were biotinylated. The beads were then reallocated to 9 reaction vessels, and the percentage of biotinylated beads to total beads in each vessel was determined by a FACS analyzer. Table 4 shows that the mixed beads in each reaction vessel have approximately the same ratio of biotinylated beads to total beads as the parent vessel.

TABLE 4

| | % Bright Beads |
|---|---|
| Parent | 9.1 |
| 1 | 9.7 |
| 2 | 9.7 |
| 3 | 9.4 |
| 4 | 8.7 |
| 5 | 9.4 |
| 6 | 8.9 |
| 7 | 9.1 |
| 8 | 8.9 |
| 9 | 9.3 |
| Average | 9.2 |
| Standard dev. | 0.32 |

8.2. Example 2

A combinatorial synthesis of YGGFL was performed using the synthesis device. The synthesis was done in reaction vessels 1–6; 7–9 were disconnected. The six amino acids added to the beads were L, E, G, Y, A, and F. YGGFL was specified along with other peptides. Beads were added to the parent vessel (29.5 mg) and suspended in DMF. Each synthesis cycle included steps of redistribution, peptide coupling, capping, amine deprotection, collection of deprotection for FMOC, rinsing with DMF, and recombination in the parent.

Following synthesis, the labelled Hertz antibody was introduced to the mixed beads. The Hertz antibody binds mostly with YGGFL. FACS analysis identified the presence of YGGFL, proving that this specified combination was synthesized by the synthesizer. The experiment shows that a diverse collection of peptides, including the YGGFL chain, can be specified and synthesized via the synthesizer.

Although the present invention has been described in some detail by way of illustration and example for purposes of clarity and understanding, it will be apparent that certain changes and modifications may be practiced within the scope of the appended claims.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A method of synthesizing diverse compounds on a plurality of substrates comprising the steps of:

a) in each of a first plurality of reaction vessels, providing a plurality of substrates;

b) delivering through a pressurized delivery means a first compound to each of said reaction vessels wherein said delivery means is coupled to each of said reaction vessels and to a mixing vessel and can deliver selected reagents to said mixing vessel or to at least one of said plurality of reaction vessels and wherein the first compound in one of said reaction vessels is different from the first compound in selected other reaction vessels;

c) in each of said reaction vessels, coupling said first compound to said substrates to produce an immobilized compound;

d) isolating said immobilized compounds in each of said reaction vessels by introducing a pressurized medium into each of said reaction vessels and allowing any fluids contained within the vessel to drain from each of said vessels; and e) transferring said immobilized compounds through a pressurized transfer means to said mixing vessel, said transfer means comprising a common manifold connected to said mixing vessel and a plurality of flow lines connecting said plurality of reaction vessels to said common manifold, wherein said transfer means is coupled to each of said reaction vessels and to said mixing vessel f) mixing said immobilized compounds;

g) redistributing said immobilized compounds through said transfer means from said mixing vessel back to said plurality of reaction vessels;

h) delivering through said pressurized delivery means a second compound to each of said reaction vessels; and i) coupling said second compound to said immobilized compounds.

2. The method of claim 1, wherein said mixing vessel, said reaction vessels, and said delivery means are sealed from the atmosphere.

3. The method of claim 1, wherein said transfer means further comprises a valve for controlling the transfer of said solid supports between said mixing vessel and said plurality of reaction vessels, said valve being the only valve through which solid supports traverse during the shift between said mixing vessel and said plurality of reaction vessels.

4. The method of claim 1, wherein after said first compound is coupled to said substrates, a first molecular tag is delivered through said delivery means to each of said reaction vessels, wherein said tag identifies the compound bound to said substrate or records a step in a synthesis of said compound.

5. The method of claim 4, wherein said tag has a recognizable feature due to a physical property of said tag, said physical property selected from the group consisting of size, shape, color, optical density, differently absorbing or emitting of light, magnetic or electronic properties; and chemical reactivity.

6. The method of claim 5, wherein said tag comprises a fluorophore.

7. The method of claim 5, wherein said tag is a nucleotide or an oligonucleotide.

8. The method of claim 4, wherein said first molecular tag is coupled to a preexisting tag.

9. The method of claim 4, wherein said preexisting tag is coupled to said substrate.

10. The method of claim 4, wherein said molecular tag is coupled to said solid support and not to another molecular tag.

11. The method of claim 4, wherein said molecular tag is coupled to a reactive group of said compound.

12. The method of claim 1, wherein said substrate is a bead or particle.

13. The method of claim 1, wherein said substrate is a nonporous bead.

14. The method of claim 1, wherein said substrate is a bead with a diameter in the range of 1 $\mu$m to 1 mm.

* * * * *